United States Patent
Chen et al.

(10) Patent No.: US 9,434,735 B2
(45) Date of Patent: Sep. 6, 2016

(54) AMORPHOUS FORM OF 4-((4-(CYCLOPENTYLOXY)-5-(2-METHYLBENZO[D]OXAZOL-6-YL)-7H-PYRROLO[2,3-D]PYRIMIDIN-2-YL)AMINO)-3-METHOXY-N-METHYLBENZAMIDE, COMPOSITIONS THEREOF AND METHODS OF THEIR USE

(71) Applicant: Signal Pharmaceuticals, LLC, San Diego, CA (US)

(72) Inventors: Ming J. Chen, West Windsor, NJ (US); Jale Muslehiddinoglu, Franklin Park, NJ (US); Alexander Ruchelman, Cream Ridge, NJ (US); Terrence Joseph Connolly, Warwick, NY (US)

(73) Assignee: Signal Pharmaceuticals, LLC, San Diego, CA (US)

( * ) Notice: Subject to any disclaimer, the term of this patent is extended or adjusted under 35 U.S.C. 154(b) by 0 days.

(21) Appl. No.: 14/797,542

(22) Filed: Jul. 13, 2015

(65) Prior Publication Data

US 2016/0009722 A1 Jan. 14, 2016

Related U.S. Application Data

(60) Provisional application No. 62/024,123, filed on Jul. 14, 2014.

(51) Int. Cl.
*C07D 487/04* (2006.01)
(52) U.S. Cl.
CPC .................................. *C07D 487/04* (2013.01)
(58) Field of Classification Search
None
See application file for complete search history.

(56) References Cited

U.S. PATENT DOCUMENTS

| | | |
|---|---|---|
| 3,507,866 A | 4/1970 | Jones et at |
| 3,567,725 A | 3/1971 | Grabowki et al. |
| 4,294,836 A | 10/1981 | Lesher et al. |
| 4,294,837 A | 10/1981 | Lesher et al. |
| 4,309,537 A | 1/1982 | Lesher et al. |
| 4,317,909 A | 3/1982 | Lesher et al. |
| 4,898,872 A | 2/1990 | Campbell et al. |
| 4,963,561 A | 10/1990 | Lesher et al. |
| 5,424,311 A | 6/1995 | Billhardt-Troughton |
| 5,869,659 A | 2/1999 | Stolle et al. |
| 6,031,105 A | 2/2000 | Wright |
| 6,093,728 A | 7/2000 | McMahon et al. |
| 6,372,740 B1 | 4/2002 | Murata et al. |
| 6,566,367 B2 | 5/2003 | Bakthavatchalam et al. |
| 6,825,184 B2 | 11/2004 | Ciriillo et al. |
| 6,855,723 B2 | 2/2005 | McMahon et al. |

(Continued)

FOREIGN PATENT DOCUMENTS

| | | |
|---|---|---|
| CA | 2 458 699 A1 | 3/2003 |
| DE | 262 026 | 11/1988 |

(Continued)

OTHER PUBLICATIONS

Barlin, "Purine analogs as amplifiers of phleomycin. VII. Some 1H-inidazo[4,5-b]pyrazines and related compound," Australian Journal of Chemistry, vol. 35, pp. 2299-2306 (1982).

(Continued)

*Primary Examiner* — Anna Pagonakis
(74) *Attorney, Agent, or Firm* — Jones Day

(57) ABSTRACT

Provided herein is an amorphous form of 4-((4-(Cyclopentyloxy)-5-(2-methylbenzo[d]oxazol-6-yl)-7H-pyrrolo[2,3-d]pyrimidin-2-yl)amino)-3-methoxy-N-methylbenzamide, compositions thereof, and methods of their use for treating or preventing a cancer, in particular solid tumors and hematological cancers as described herein.

5 Claims, 11 Drawing Sheets

(56) References Cited

U.S. PATENT DOCUMENTS

| | | |
|---|---|---|
| 7,199,119 B2 | 4/2007 | Burkitt et al. |
| 7,247,621 B2 | 7/2007 | Hong et al. |
| 7,429,572 B2 | 9/2008 | Clark |
| 7,476,665 B2 | 1/2009 | Burgey |
| 7,608,622 B2 | 10/2009 | Liu et al. |
| 7,902,187 B2 | 3/2011 | Neagu et al. |
| 7,919,490 B2 | 4/2011 | Neagu et al. |
| 7,968,556 B2 | 6/2011 | Mortensen et al. |
| 7,981,893 B2 | 7/2011 | Mortensen et al. |
| 8,110,578 B2 | 2/2012 | Perrin-Ninkovic et al. |
| 8,268,809 B2 | 9/2012 | Kalman |
| 8,372,976 B2 | 2/2013 | Mortensen et al. |
| 8,383,634 B2 | 2/2013 | Mortensen et al. |
| 8,492,381 B2 | 7/2013 | Perrin-Ninkovic et al. |
| 8,507,492 B2 | 8/2013 | Perrin-Ninkovic et al. |
| 8,569,494 B2 | 10/2013 | Harris et al. |
| 8,642,660 B2 | 2/2014 | Goldfard |
| 9,040,547 B2 | 5/2015 | Cheng et al. |
| 9,155,736 B2 | 10/2015 | Xu et al. |
| 2004/0063658 A1 | 4/2004 | Roberts et al. |
| 2004/0213757 A1 | 10/2004 | Zhu et al. |
| 2006/0004014 A1 | 1/2006 | Hoffmann et al. |
| 2006/0142269 A1 | 6/2006 | Dykes |
| 2009/0281075 A1 | 11/2009 | Roughton et al. |
| 2010/0144738 A1 | 6/2010 | Bornmann et al. |
| 2011/0257167 A1 | 10/2011 | Chopra et al. |
| 2012/0028972 A1 | 2/2012 | Wong |
| 2013/0102613 A1 | 4/2013 | Xu et al. |
| 2013/0142873 A1 | 6/2013 | Assaf et al. |
| 2013/0158023 A1 | 6/2013 | Ning et al. |
| 2013/0225518 A1 | 8/2013 | Xu et al. |
| 2013/0245026 A1 | 9/2013 | Xu et al. |
| 2013/0245028 A1 | 9/2013 | Xu et al. |
| 2013/0245029 A1 | 9/2013 | Xu et al. |
| 2014/0113904 A1 | 4/2014 | Mortensen et al. |
| 2014/0200206 A1 | 7/2014 | Calabrese et al. |

FOREIGN PATENT DOCUMENTS

| | | |
|---|---|---|
| EP | 0 385 850 | 9/1990 |
| JP | 63275582 | 5/1987 |
| JP | 2001048882 | 2/2001 |
| JP | 2002100363 | 4/2002 |
| JP | 2002167387 | 6/2002 |
| WO | WO 99/16438 | 4/1999 |
| WO | WO 99/28320 | 6/1999 |
| WO | WO 00/73306 | 12/2000 |
| WO | WO 02/48152 | 6/2002 |
| WO | WO 02/076954 | 10/2002 |
| WO | WO 03/032989 | 4/2003 |
| WO | WO 03/093290 | 11/2003 |
| WO | WO 2004/042002 | 5/2004 |
| WO | WO 2004/065378 | 8/2004 |
| WO | WO 2004/076454 | 9/2004 |
| WO | WO 2004/085409 | 10/2004 |
| WO | WO 2005/003147 | 1/2005 |
| WO | WO 2005/120511 | 12/2005 |
| WO | WO 2006/001266 | 1/2006 |
| WO | WO 2006/030031 | 3/2006 |
| WO | WO 2006/036883 | 4/2006 |
| WO | WO 2006/045828 | 5/2006 |
| WO | WO 2006/050076 | 5/2006 |
| WO | WO 2006/065703 | 6/2006 |
| WO | WO 2006/087530 | 8/2006 |
| WO | WO 2006/091737 | 8/2006 |
| WO | WO 2006/108103 | 10/2006 |
| WO | WO 2008/016669 | 2/2008 |
| WO | WO 2008/051493 | 5/2008 |
| WO | WO 2008/051494 | 5/2008 |
| WO | WO 2009/126926 | 10/2009 |
| WO | WO 2009/131687 | 10/2009 |
| WO | WO 2010/062571 | 6/2010 |
| WO | WO 2010/068483 | 6/2010 |
| WO | WO 2011/097333 | 8/2011 |
| WO | WO 2013/042006 | 3/2013 |
| WO | WO 2014/025486 | 2/2014 |

OTHER PUBLICATIONS

Beresnev et al., "Interaction of 5-methoxy-1,2,4-traizines with uras as a new route to 6-azapurines," Medeleev Commu., vol. 2, pp. 58-59 (2000).

Bergmann et al., "2-Phenylpurines, their chemical and enzumological reactivity," J. Chem Org., pp. 3729-3735 (1963).

Booth et al., "Synthesis of 9-Hydroxyalkyl-substituted purines from the corresponding 4-(C-Cyanoformimidoyl)imidazole-5-amines," J, Chem Society, Perkin Transactions 1: Organic and Bio-Organic Chemstry, vol. pp. 2119-2126 (1992).

Booth et al., "Synthesis of [1α, 2β,3α-2,3-bis(benzyloxymethyl)cyclobut1]imidazol-5-amines: important precursors to cyclobut-A derivatives," J. Chem Society, Perkin Tranactions 1: Organic and Bio-Organic Chemistry, vol. 6, pp. 669-675 (1995).

Booth et al., "The Reactions of Diaminomaleonitrile with Isocyanates and Either Aldehydes or Ketones Revisited," J. Org Chem, vol. 66, pp. 8436-8441 (2001).

Booth, et al., "Synthesis of 4- and 5-Disubstituted 1-Benzylimidazoles, Important Precursors of Purine Analogs," J. of Heterocyclic of Chemistry, vol. 31(2), pp. 345-350 (1994).

Chupakhin et al., "A simple one pot synthesis of condensed 1,2,4-triazines by using the tandem $A_N$-$S_N$ipso and $S_N^H$—$S_N$ipso reactions," J. of Heterocyclic Chemistry, vol. 38(4), pp. 901-907 (2001).

Cohen, "The role of protein phosphorylation in human health and disease," Eur. J. Biochem, vol. 268, pp. 5001-5010 (2001).

Cohen, P. "Protein kinases—the major drug targets of the twenty-first century?" Nature Reviews/Drug Discovery, vol. 1, pp. 309-315 (2002).

Coish, et al., "Small molecule inhibitors of IKK kinase activity," Expert Opin. Ther. Patents, vol. 16(1), pp. 1-12 (2006).

Costa et al., "Aspects of mTOR biology and the use of mTOR inhibitors in non-Hodgkin's lymphoma," Cancer Treatment Reviews, Saunders, US, vol. 33(1), pp. 78-84 (2007).

Crofts et al., "Metabolism of 2-amino-1-methyl-6-phenylimidazo[4,5-b]pyridine (PhIP) by human cytochrome P4501B1," Carcinogenesis, vol. 18(9), pp. 1793-1798 (1997).

Dang et al., "Efficient synthesis of purines and purine nucleosides via an inverse electron demand diels—alder reaction," J. Am Chem Soc., vol. 121(24), pp. 5833-5834 (1999).

Database Caplus Online Chemical Abstracts Service, Columbus, Ohio, Database Accession No. 1951:49974 (XP-002472261) (1951).

Database Caplus Online Chemical Abstracts Service, Columbus, Ohio, Database Accession No. 1978:433195 (XP-002472262) (1978).

Database Caplus Online Chemical Abstracts Service, Columbus, Ohio, Database Accession No. 1966:26849 (XP-002472263) (1965).

Dornow et al., "Synthese von2-Oxy-imidazolo-(5',4':2,3)-pyridinen)," Arch Pharm. vol. 290, pp. 20-31 (1957) (w/English language abstract).

Dorwald F. Zaragoza, "Side Reactions in Organic Synthesis: A Guide to Successful Synthesis Design," Weinheim: Wiley-VCH Verlag GmbH & Co. KgaA, Preface. (2005).

Dzierba et al., "Synthesis, structure-activity relationships, and in vivo properties of 3,4-dihydro-1H-pyrido[2,3-b]pyrazin-2-ones as corticotropin-releasing factor-1 receptor antagonists," J of Medicinal Chemistry, vol. 47(23), pp. 5783-5790 (2004).

EPO Supplementary European Search Report dated Feb. 8, 2013 issued in connection with PCT/US2010/053678.

Fabbro et al., "Protein kinases as targets for anticancer agents: from inhibitors touseful drugs," Pharmacology & Therapeutics, vol. 93, pp. 79-98 (2002).

Farhadi et al., "The role of protein kinase C isoforms in modulating injury and repair of the intestinal barrier," J. Pharm Exp. Ther., vol. 316(1), pp. 1-7 (2006).

(56) References Cited

OTHER PUBLICATIONS

Frandsen et al., "Reaction of the N2-acetoxy derivative of 2-amino-1-methyl-6-phenylimidazo[4,5,b] pyridine . . . ," Carcinogenesis, vol. 13(4), pp. 629-635 (1992).
Frost et al., "AKT activity regulates the ability of mTOR inhibitors to prevent angiogenesis and VEGF expression in multiple myeloma cells," Oncogene, vol. 26(16), pp. 2255-2262 (2007).
Georgakis and Younes, "From rapi nui to rapamycin: targeting PI3K/Akt/mTOR for cancer therapy," Expert Rev. Anticancer Ther., vol. 6(1), 131-140 (2006).
Hamad, "A new synthesis of 4-cyano-1,3-dihydro-2-oxo-2H-imidazole-5-($N^1$-tosyl)carboxamide: Reactive precursor for thiopurine analogues," J of Heterocyclic Chemistry, vol. 38(4), pp. 939-944 (2001).
Product specification of "Bis(di-tert-butyl(4-dimethylaminophenyl)phosphine)dichloropalladium(II)" from SIGMA-ALDRICH: http://www.sigmaaldrich.com/catalog/product/ALDRICH/678740?lang=en&region=US, last accessed Nov. 1, 2012.
Product specification of "[1,1'-Bis(di-tert-butylphosphino)ferrocene]dichloropalladium(II)" from SIGMA-ALDRICH: http://www.sigmaaldrich.com/catalog/product/ALDRICH/701602?lang=en&region=US#, last accessed Nov. 1, 2012.
Product specification of "[1,1'-Bis(diphenylphosphino)ferrocene]dichloropalladium(II)" from SIGMA-ALDRICH:http://www.sigmaaldrich.com/catalog/product/aldrich/697230?lang=en&region=US, last accessed Nov. 1, 2012.
"Application Guide for Palladium Catalyzed Cross-Coupling Reactions" http://www.sigmaaldrich.com/chemistiy/chemical-synthesis/technology-spotlights/catalysisapplicationguide.html, last accessed Nov. 1, 2012.
Irie et al., "Toward the development of new medicinal leads with selectivity for protein kinase C isozymes," The Chemical Record, vol. 5, pp. 185-195 (2005).
Itoh et al., "A novel practical synthesis of C-2-arylpurines," Advanced Synthesis & Catalysis, vol. 346, pp. 1859-1867 (2004).
Gulati et al. "Involvement of mTORC1 and mTORC2 in regulation of glioblastoma multiforme growth and motility," International Journal of Oncology, vol. 35(4) (2009), abstract.
Jones et al., "6-Substituted-5-chloro-1,3-dihydro-2H-imidazo(4,5-b)pyrazin-2-ones with hypotensive activity," J. Med. Chem., vol. 16(5), pp. 537-542 (1973).
Jordan, V.C., Nature Reviews: Drug Discover, vol. 2, p. 205 (2003).
Kazaoka et al., "Synthesis of 6-substituted 9-benzyl-8-hydroxypurines with potential interferon-indcuing activity," Chemical & Pharmaceutical Bulletin, vol. 51(5), pp. 608-611 (2003).
Killday et al., "Microxine, a new cdc2 kinase inhibitor from the Australian marine sponge *Microxina* species," J. of Natural Products, vol. 64(4), pp. 525-526 (2001).
Minehan et al., "Molecular recognition of DNA by Hoechst Benzimidazoles: Exploring beyond theopyrrole-imidazole-hydroxypyrrole polyamide-pairing code," Helvitica Chima Acta, vol. 83(9), pp. 2197-2213 (2000).
Mortensen et al., "Discovery and SAR exploration of a novel series of imidazo[4,5-] pyrazin-2-ones as potent and selective mTOR kinase inhibitors," Bioorganic & Medicinal Chemistry Letters, Pergamon, Elsevier Science, GB, vol. 21(22), pp. 6793-6799 (2011).
Nagashima et al., "Solution-Phase parallel synthesis of an N-Alkylated dihydropteridinone library from fluorous amino acids," J of Comb. Chemistry, vol. 6(6), pp. 942-949 (2004).
Park et al., "A novel mechanism of TRAF signaling revealed by structural and functional analyses of the TRADD-TRAF2 interaction," Cell, vol. 101, pp. 777-787 (2000).
Patani et al., "Bioisosterim: A rational approach in drug design," Chemical Reviews, vol. 96, pp. 3147-3176 (1996).
Registry File Document for RN 863501-03-5, 863502-39-0 Sep. 20, 2005.
Seela et al., "Product Class 17: Purines," Science of Synthesis, vol. 16, pp. 945-1108 (2004).
Singh et al., 1994, "Novel cAMP PDE III Inhibitors: Imidazo[4,5-b]pyridin-2(3H)-ones and Thiazolo[4,5-b]pyridin-2(3h)-ones and Their Analogs," J. Med. Chem, vol. 37(2):248-254.
Sridhar et al., "Protein Kinasesas Therapeutic Targets," Pharm. Research, vol. 17(11), pp. 1345-1353 (2000).
Office Action mailed Jun. 11, 2009 for U.S. Appl. No. 11/975,652.
Office Action mailed Sep. 2, 2009 for U.S. Appl. No. 11/975,652.
Final Office Action mailed Feb. 2, 2010 for U.S. Appl. No. 11/975,652 with Notice of References Cited.
Office Action mailed May 12, 2010 for U.S. Appl. No. 11/975,652.
Final Office Action mailed Sep. 30, 2010 for U.S. Appl. No. 11/975,652 with Notice of References Cited.
PCT International Search Report dated Mar. 29, 2010 issued in connection with PCT/US2009/062143.
PCT Written Opinion of the International Searching Authority dated Mar. 29, 2010.
Office Action mailed Nov. 10, 2010 for U.S. Appl. No. 12/605,791.
PCT IPRP with Written Opinion of the International Searching Authority dated May 12, 2011 in connection with PCT /US2009/062143.
Office Action mailed Jan. 19, 2011 for U.S. Appl. No. 12/605,791 with Notice of References Cited.
Final Office Action mailed May 10, 2011 for U.S. Appl. No. 12/605,791.
Advisory Action mailed Aug. 17, 2011 for U.S. Appl. No. 12/605,791.
Advisory Action mailed Sep. 14, 2011 for U.S. Appl. No. 2/605,791.
PCT International Search Report dated Dec. 27, 2010 issued in connection with PCT/US2010/053678.
PCT Written Opinion dated Dec. 27, 2010 in connection with PCT/US/10/53678.
Office Action mailed Feb. 28, 2012 for U.S. Appl. No. 12/910,920 with Notice of Reference Cited.
PCT IPRP dated May 10, 2012 issued in connection with PCT/US2010/053678.
Office Action mailed Jun. 28, 2012 for U.S. Appl. No. 12/910,920 with Notice of Reference Cited.
Final Office Action mailed Nov. 6, 2012 for U.S. Appl. No. 12/910,920 with Notice of Reference Cited.
Office Action mailed Apr. 2, 2012 for U.S. Appl. No. 13/295,513.
Office Action mailed Aug. 27, 2012 for U.S. Appl. No. 13/295,513 with Notice of References Cited.
PCT Partial International Search dated Feb. 21, 2013 issued in connection with PCT/US2012/060723.
PCT International Search Report dated Feb. 13, 2013 issued in connection with PCT/US2012/067172.
PCT Written Opinion dated Feb. 13, 2013 issued in connection with PCT/US/2012/067172.
Vippagunta et al., Advanced Drug Delivery Reviews, vol. 48, pp. 3-26 (2001) (Cited in Office Action in connection with U.S. Appl. No. 12/605,791).
Wallace, "Palladium-catalyzed synthesis of quinoxaline derivatives," Tetrahedron, vol. 64, pp. 9675-9684 (2008).
Westover et al., "Synthesis and antiviral activity of certain 9-β-D-Riofuranoaylpurine-6-carboxamides," J.Med. Chem., vol. 24(8), pp. 941-946 (1981).
Wolff, Manfred E., Ed. Burger's Medicinal Chemistry and Drug Discovery—Fifth Edition, New York: John Wiley & Sons, vol. 1, pp. 975-976 (1996).
Yoneda et al., "A transformation of 7-azapteridines into 6-azapurines (Imidazo[4,5-e]-as-triazines)," Heterocycles, vol. 4(9), pp. 1503-1508 (1976).
Yoneda et al., "Synthesis of imadazo[4,5-e]-as-triazine (6-Azapurine) Deriviatives," Chem & Pharm Bulletin, vol. 26(10), pp. 3154-3160 (1978).
Zaki et al., "The synthesis of imidazol[4,5-d]pyridines from a substituted imidazole and acyl or sulfonyl acetonitrile," Tetrahedron, vol. 63(18), pp. 3745-3753 (2007).
PCT Partial International Search dated Nov. 15, 2012 issued in connection with PCT/US2012/049281.
PCT International Search Report dated Jan. 11, 2013 issued in connection with PCT/US2012/049281.

(56) References Cited

OTHER PUBLICATIONS

PCT Written Opinion dated Feb. 13, 2013 issued in connection with PCT/US2012/049281.
Yuan et al., "Targeting tumorigenesis: development and use of mTOR inhibitors in cancer therapy," Journal of Hematology & Oncology, vol. 2(1), p. 45 (2009).
Carretero et al., "Integrative Genomic and Proteomic Analyses Identify Targets for Lkb1-Deficient Metastatic Lung Tumors," Cancer Cell, vol. 17( 6), pp. 547-559 (2010).
Gao et al., "LKB1 in lung cancerigenesis: a serine/threonine kinase as tumor suppressor," Protein & Cell, vol. 2(2), pp. 99-107 (2011).
Gao et al., "LKB1 inhibits lung cancer progression through lysyl oxidase and extracellular matrix remodeling," Proceedings of the National Academy of Sciences, vol. 107(44), pp. 18892-18897 (2010).
Inge et al., " Expression of LKB1 tumor suppressor in non-small cell lung cancer determines sensitivity to 2-deoxyglucose," Journal of Thoracic and Cardiovascular Surgery, vol. 137(3), pp. 580-558 (2009).
Wingo et al., "Somatic LKB1 Mutations Promote Cervical Cancer Progression," Plos One, vol. 4(4), pp. 5137-5138 (2009).
Shaw et al., "The LKB1 tumor suppressor negatively regulates mTOR signaling," Cancer Cell, vol. 6(1), pp. 91-99 (2004).
Huang et al., "Genetic and epigenetic silencing of SCARA5 may contribute to human hepatocellular carcinoma by activating FAK signaling," Journal of Clinical Investigation, vol. 120(1), pp. 223-241 (2010).
Brenner et al., "Mechanistic Rationale for Inhibition of Poly(ADP-Ribose) Polymerase in ETS Gene Fusion-Positive Prostate Cancer," Cancer Cell, vol. 19, pp. 664-678 (2011).
Brenner et al., "PARP-1 Inhibition as a Targeted Strategy to Treat Ewing's Sarcoma," Cancer Res vol. 72, pp. 1608-1613 (2012).
Dey et al., "Preclinical efficacy of a dual PI3K-mTOR inhibitor, BEZ235 in triple negative breast cancer," European Journal of Cancer, vol. 47, No. Suppl. 4, Oct. 2011, p. 517.
Johnston, "Are we missing the mTOR target in breast cancer?," Breast Cancer Research and Treatment, Kluwer Academic Publishers, Bolivia, vol. 128, No. 3, Oct. 16, 2010, pp. 607-611.
Lehmann et al., "Identification of human triple-negative breast cancer subtypes and preclinical models for selection of targeted therapies," The Journal of Clinical Investigation, Jul. 2011, vol. 121, No. 7, Jul. 2011, pp. 2750-2767.
Liu et al., "Combinatorial Effects of Lapatinib and Rapamycin in Triple-Negative Breast Cancer Cells," Molecular Cancer Therapeutics, vol. 10, No. 8, Aug. 1, 2011, pp. 1460-1469.
Lori Berk et al., "Analysis of the pharmacodynamic activity of the mTOR inhibitor ridaforolimus (AP23573, MK-8669) in a phase 1 clinical trial," Cancer Chemotherapy and Pharmacology, Springer, Berlin, Germany, vol. 69, No. 5, Jan. 10, 2012, pp. 1369-1377.
Macaskill et al., "The mammalian target of rapamycin inhibitor everolimus (RAD001) in early breast cancer: results of a pre-operative study," Breast Cancer Research and Treatment, Kluwer Academic Publishers, Bolivia, vol. 128, No. 3, Oct. 13, 2010, pp. 725-734.
Sanchez et al., "Preclinical modeling of combined phosphatidylinositol-3-kinase inhibition with endocrine therapy for estrogen receptor-positive breast cancer," Breast Cancer Research, Current Science, London, United Kingdom, vol. 13, No. 2, Mar. 1, 2011, p. R21.
Toft et al., "Minireview: Basal-Like Breast Cancer: From Molecular Profiles to Targeted Therapies," Molecular Endocrinology, vol. 25, No. 2, Feb. 1, 2011, pp. 199-211.
Zeng et al., "Treating triple-negative breast cancer by a combination of rapamycin and cyclophosphamide: An in vivo bioluminescence imaging study," European Journal of Cancer, Pergamon Press, Oxford, United Kingdom, vol. 46, No. 6, Apr. 1, 2010, pp. 1132-1143.
Zhao et al., "The effect of mTOR inhibition alone or combined with MEK inhibitors on brain metastasis: an in vivo analysis in triple-negative breast cancer models," Breast Cancer Research and Treatment, Kluwer Academic Publishers, Bolivia, vol. 131, No. 2, Mar. 11, 2011, pp. 425-436.

AMORPHOUS FORM OF 4-((4-(CYCLOPENTYLOXY)-5-(2-METHYLBENZO[D]OXAZOL-6-YL)-7H-PYRROLO[2,3-D]PYRIMIDIN-2-YL)AMINO)-3-METHOXY-N-METHYLBENZAMIDE, COMPOSITIONS THEREOF AND METHODS OF THEIR USE

This application claims the benefit of U.S. Provisional Application No. 62/024,123, filed Jul. 14, 2014, the entire contents of which are incorporated herein by reference.

1. FIELD

Provided herein is an amorphous form of 4-((4-(Cyclopentyloxy)-5-(2-methylbenzo[d]oxazol-6-yl)-7H-pyrrolo[2,3-d]pyrimidin-2-yl)amino)-3-methoxy-N-methylbenzamide, compositions thereof, and methods of their use for treating or preventing a cancer, in particular solid tumors and hematological cancers as described herein as well as the amorphous form of 4-((4-(Cyclopentyloxy)-5-(2-methylbenzo[d]oxazol-6-yl)-7H-pyrrolo[2,3-d]pyrimidin-2-yl) amino)-3-methoxy-N-methylbenzamide and compositions thereof for use in these methods.

2. BACKGROUND

2.1 Solid Forms of Pharmaceutical Compounds

The identification and selection of a solid form of a pharmaceutical compound are complex, given that a change in solid form may affect a variety of physical and chemical properties, which may provide benefits or drawbacks in processing, formulation, stability, bioavailability, storage, handling (e.g., shipping), among other important pharmaceutical characteristics. Amorphous solids are characterized by a lack of long-range structural order, whereas crystalline solids are characterized by structural periodicity.

Notably, it is not possible to predict a priori if crystalline forms of a compound even exist, let alone how to successfully prepare them (see, e.g., Braga and Grepioni, 2005, "Making crystals from crystals: a green route to crystal engineering and polymorphism," *Chem. Commun.*: 3635-3645 (with respect to crystal engineering, if instructions are not very precise and/or if other external factors affect the process, the result can be unpredictable); Jones et al., 2006, Pharmaceutical Cocrystals: An Emerging Approach to Physical Property Enhancement," *MRS Bulletin* 31:875-879 (At present it is not generally possible to computationally predict the number of observable polymorphs of even the simplest molecules); Price, 2004, "The computational prediction of pharmaceutical crystal structures and polymorphism," *Advanced Drug Delivery Reviews* 56:301-319 ("Price"); and Bernstein, 2004, "Crystal Structure Prediction and Polymorphism," *ACA Transactions* 39:14-23 (a great deal still needs to be learned and done before one can state with any degree of confidence the ability to predict a crystal structure, much less polymorphic forms)).

The compound chemically named 4-((4-(cyclopentyloxy)-5-(2-methylbenzo[d]oxazol-6-yl)-7H-pyrrolo[2,3-d]pyrimidin-2-yl)amino)-3-methoxy-N-methylbenzamide and tautomers thereof (collectively referred to herein as "Compound 1") are disclosed in U.S. patent application Ser. No. 14/155,485, filed on Jan. 15, 2014, the entirety of which is incorporated by reference herein.

2.2 Cancer

Cancer is characterized primarily by an increase in the number of abnormal cells derived from a given normal tissue, invasion of adjacent tissues by these abnormal cells, or lymphatic or blood-borne spread of malignant cells to regional lymph nodes and to distant sites (metastasis). Clinical data and molecular biologic studies indicate that cancer is a multistep process that begins with minor pre-neoplastic changes, which may under certain conditions progress to neoplasia. The neoplastic lesion may evolve clonally and develop an increasing capacity for invasion, growth, metastasis and heterogeneity, especially under conditions in which the neoplastic cells escape the host's immune surveillance. See Roitt, I., Brostoff, J and Kale, D., Immunology, 17.1-17.12 (3rd ed., Mosby, St. Louis, Mo., 1993).

Cancers figure among the leading causes of death worldwide, accounting for 8.2 million deaths in 2012. It is expected that annual cancer cases will rise from 14 million in 2012 to 22 million within the next two decades. See Cancer Fact sheet N°297, World Health Organization, February 2014, retrieved 10 Jun. 2014 and Globocan 2012, IARC.

The current drugs used in cancer treatment are highly toxic and often non-specific. Current anticancer therapy strategies are typically focused on rapid proliferating cells, which can shrink primary and metastatic tumors, but such effects are usually transient and tumor relapse of most metastatic cancers frequently occur. One possible reason for failure is the existence of cancer stem cells. Unlike most cells within the tumor, cancer stem cells are resistant to well-defined chemotherapy and after treatment, they can regenerate all the cell types in the tumor through their stem cell-like behavior of largely quiescent nature and their abundant expression of drug transporters.

There is an enormous variety of cancers which are described in detail in the medical literature. The incidence of cancer continues to climb as the general population ages, as new cancers develop, and as susceptible populations (e.g., people infected with AIDS or excessively exposed to sunlight) grow. However, options for the treatment of cancer are limited. A tremendous demand therefore exists for new methods and compositions that can be used to treat patients with cancer.

Citation or identification of any reference in Section 2 of this application is not to be construed as an admission that the reference is prior art to the present application.

3. SUMMARY

Provided herein is an amorphous form of Compound 1:

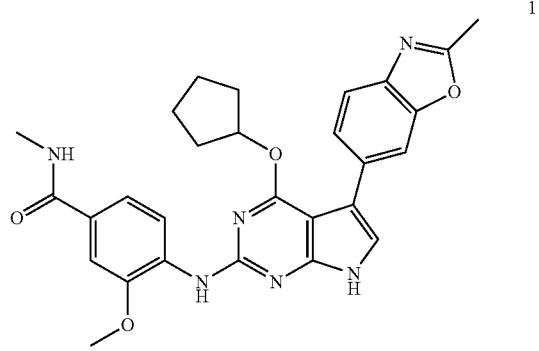 [SMILES: CNC(=O)c1ccc(Nc2nc(OC3CCCC3)c3c(-c4ccc5nc(C)oc5c4)c[nH]c3n2)c(OC)c1]

having the name 4-((4-(Cyclopentyloxy)-5-(2-methylbenzo[d]oxazol-6-yl)-7H-pyrrolo[2,3-d]pyrimidin-2-yl) amino)-3-methoxy-N-methylbenzamide, including tautomers thereof. Also provided are methods of preparing, isolating and characterizing the amorphous form.

Provided herein are methods of treating a cancer, in particular a solid tumor or a hematological cancer, comprising administering to a subject in need thereof an effective amount of an amorphous form of Compound 1.

Also provided herein are methods for preventing cancer metastasis, comprising administering to a subject in need thereof an effective amount of an amorphous form of Compound 1. Additionally, provided herein are methods of eradicating cancer stem cells in a subject, comprising administering to a subject in need thereof an effective amount of an amorphous form of Compound 1. Also provided are methods of inducing differentiation in cancer stem cells in a subject, comprising administering to a subject in need thereof an effective amount of an amorphous form of Compound 1. In another aspect, provided are methods of inducing cancer stem cell death in a subject, comprising administering to a subject in need thereof an effective amount of an amorphous form of Compound 1.

In one aspect, provided herein are methods for treating or preventing breast cancer, in particular triple negative breast cancer (TNBC), comprising administering to a subject in need thereof an effective amount of an amorphous form of Compound 1 as described herein.

In another aspect, provided herein are methods for treating a cancer provided herein, comprising administering to a subject in need thereof an effective amount of an amorphous form of Compound 1 as described herein and a pharmaceutically acceptable carrier, excipient or vehicle.

In another aspect, provided herein are methods for preventing a cancer provided herein, comprising administering to a subject in need thereof an effective amount of an amorphous form of Compound 1 as described herein and a pharmaceutically acceptable carrier, excipient or vehicle.

The present embodiments can be understood more fully by reference to the detailed description and examples, which are intended to exemplify non-limiting embodiments.

4. BRIEF DESCRIPTION OF THE DRAWINGS

5. DETAILED DESCRIPTION 5.1 Definitions

Figure 1:
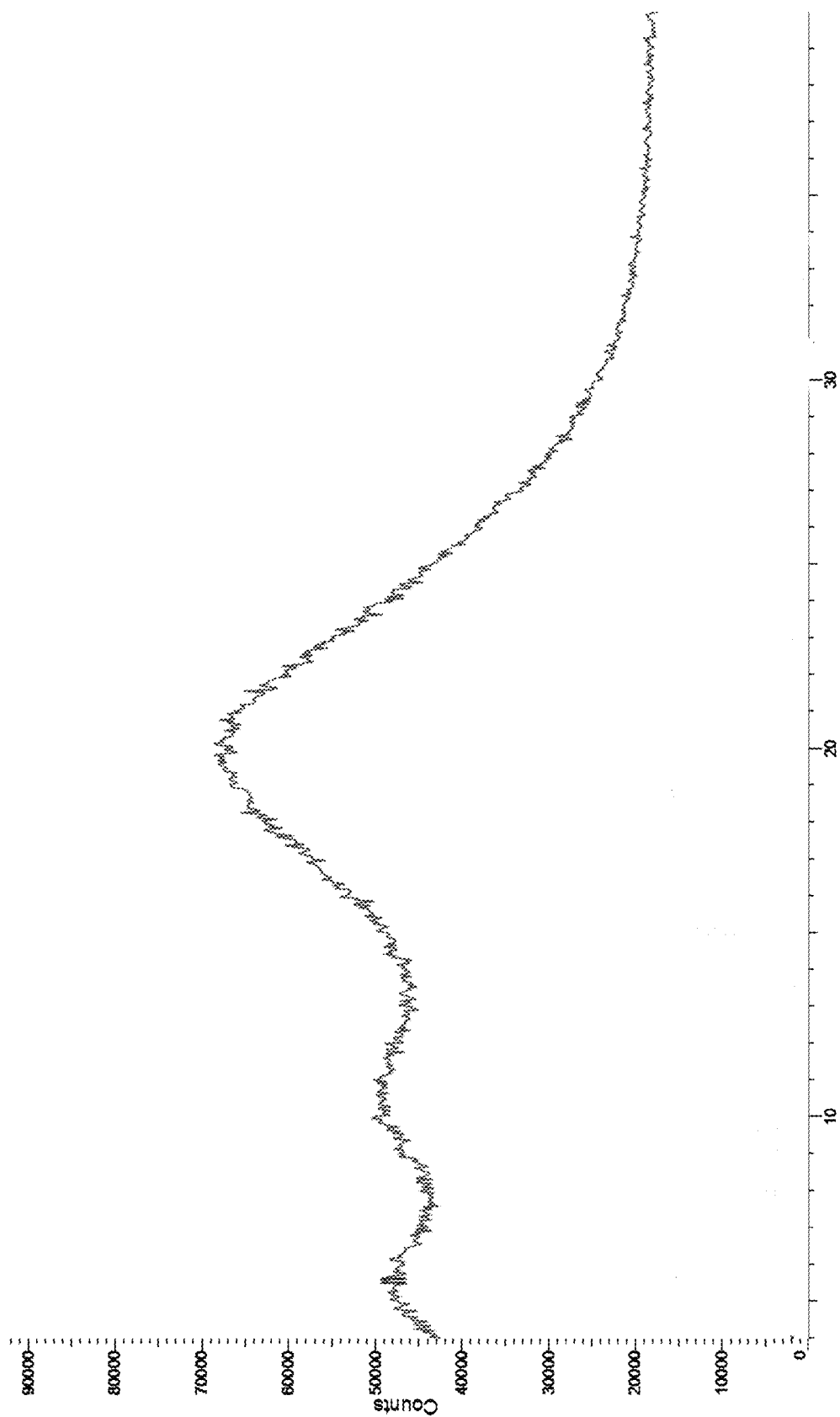
FIG. 1 depicts an XRPD pattern of the amorphous form of Compound 1.

As used herein, and unless otherwise specified, the terms "about" and "approximately," when used in connection with doses, amounts, or weight percents of ingredients of a composition or a dosage form, mean a dose, amount, or weight percent that is recognized by one of ordinary skill in the art to provide a pharmacological effect equivalent to that obtained from the specified dose, amount, or weight percent. In certain embodiments, the terms "about" and "approximately," when used in this context, contemplate a dose, amount, or weight percent within 30%, within 20%, within 15%, within 10%, or within 5%, of the specified dose, amount, or weight percent.

As used herein, and unless otherwise specified, the terms "about" and "approximately," when used in connection with a numeric value or range of values which is provided to characterize an amorphous form, e.g., a specific temperature or temperature range, such as, for example, that describes a melting, dehydration, desolvation, or glass transition temperature; a mass change, such as, for example, a mass change as a function of temperature or humidity; a solvent or water content, in terms of, for example, mass or a percentage; or a peak position, such as, for example, in analysis by, for example, IR or Raman spectroscopy or XRPD; indicate that the value or range of values may deviate to an extent deemed reasonable to one of ordinary skill in the art while still describing the solid form. Techniques for characterizing crystal forms and amorphous forms include, but are not limited to, thermal gravimetric analysis (TGA), differential scanning calorimetry (DSC), X-ray powder diffractometry (XRPD), single-crystal X-ray diffractometry, vibrational spectroscopy, e.g., infrared (IR) and Raman spectroscopy, solid-state and solution nuclear magnetic resonance (NMR) spectroscopy, optical microscopy, hot stage optical microscopy, scanning electron microscopy (SEM), electron crystallography and quantitative analysis, particle size analysis (PSA), surface area analysis, solubility studies, and dissolution studies. In certain embodiments, the terms "about" and "approximately," when used in this context, indicate that the numeric value or range of values may vary within 30%, 20%, 15%, 10%, 9%, 8%, 7%, 6%, 5%, 4%, 3%, 2%, 1.5%, 1%, 0.5%, or 0.25% of the recited value or range of values. For example, in some embodiments, the value of an XRPD peak position may vary by up to ±0.2° 2θ while still describing the particular XRPD peak.

As used herein, and unless otherwise specified, an amorphous form that is "substantially physically pure" is substantially free from other solid forms, such as crystalline forms. In certain embodiments, an amorphous form that is substantially physically pure contains less than about 10%, 9%, 8%, 7%, 6%, 5%, 4%, 3%, 2%, 1%, 0.5%, 0.4%, 0.3%, 0.2%, 0.1%, 0.05%, or 0.01% of one or more other solid forms on a weight basis. The detection of other solid forms can be accomplished by any method apparent to a person of ordinary skill in the art, including, but not limited to, diffraction analysis, thermal analysis, elemental combustion analysis, spectroscopic analysis, scanning electron microscopy (SEM) and/or X-ray powder diffraction (XRPD). In certain embodiment, provided herein is an amorphous form of Compound 1 that is substantially physically pure.

As used herein, and unless otherwise specified, an amorphous form that is "substantially chemically pure" is substantially free from other chemical compounds (i.e., chemical impurities). In certain embodiments, an amorphous form that is substantially chemically pure contains less than about 10%, 9%, 8%, 7%, 6%, 5%, 4%, 3%, 2%, 1%, 0.5%, 0.4%, 0.3%, 0.2%, 0.1%, 0.05%, or 0.01% of one or more other chemical compounds on a weight basis. The detection of other chemical compounds can be accomplished by any method apparent to a person of ordinary skill in the art, including, but not limited to, methods of chemical analysis, such as, e.g., mass spectrometry analysis, spectroscopic analysis, thermal analysis, elemental combustion analysis and/or chromatographic analysis. In certain embodiment, provided herein is an amorphous form of Compound 1 that is substantially chemically pure.

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution. For example, in aqueous solution, pyrazoles may exhibit the following isomeric forms, which are referred to as tautomers of each other:

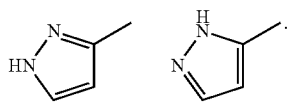

As readily understood by one skilled in the art, a wide variety of functional groups and other structures may exhibit tautomerism and all tautomers of Compound 1 are within the scope of the present invention.

Unless otherwise specified, the term "composition" as used herein is intended to encompass a product comprising the specified ingredient(s) (and in the specified amount(s), if indicated), as well as any product which results, directly or indirectly, from combination of the specified ingredient(s) in the specified amount(s). By "pharmaceutically acceptable," it is meant a diluent, excipient, or carrier in a formulation must be compatible with the other ingredient(s) of the formulation and not deleterious to the recipient thereof.

The term "solid form" refers to a physical form which is not predominantly in a liquid or a gaseous state.

As used herein and unless otherwise specified, the term "crystalline" when used to describe a compound, substance, modification, material, component or product, unless otherwise specified, means that the compound, substance, modification, material, component or product is substantially crystalline as determined by X-ray diffraction. See, e.g., Remington: The Science and Practice of Pharmacy, 21st edition, Lippincott, Williams and Wilkins, Baltimore, Md. (2005); The United States Pharmacopeia, $23^{rd}$ ed., 1843-1844 (1995).

Unless otherwise specified, the term "amorphous" or "amorphous form" means that the substance, component, or product in question is not substantially crystalline as determined by X-ray diffraction. In particular, the term "amorphous form" describes a disordered solid form, i.e., a solid form lacking long range crystalline order. In certain embodiments, an amorphous form of a substance may be substantially free of other amorphous forms and/or crystal forms. In certain embodiments, an amorphous form of a substance may contain less than about 1%, less than about 2%, less than about 3%, less than about 4%, less than about 5%, less than about 10%, less than about 15%, less than about 20%, less than about 25%, less than about 30%, less than about 35%, less than about 40%, less than about 45%, or less than about 50% by weight of one or more other amorphous forms and/or crystal forms on a weight basis. In certain embodiments, an amorphous form of a substance may be physically and/or chemically pure. In certain embodiments, an amorphous form of a substance be about 99%, about 98%, about 97%, about 96%, about 95%, about 94%, about 93%, about 92%, about 91%, or about 90% physically and/or chemically pure. In certain embodiments, the amorphous form of Compound 1 provided herein does not have any crystallinity as determined by X-ray diffraction.

"Treating" as used herein, means an alleviation, in whole or in part, of a disorder, disease or condition, or one or more of the symptoms associated with a disorder, disease, or condition, or slowing or halting of further progression or worsening of those symptoms, or alleviating or eradicating the cause(s) of the disorder, disease, or condition itself. In one embodiment, the disorder is a cancer, in particular, a solid tumor or hematological cancer. In some embodiments, "treating" means an alleviation, in whole or in part, of a cancer, or symptoms associated with a cancer, in particular, a solid tumor or hematological cancer, or a slowing, or halting of further progression or worsening of those symptoms.

"Preventing" as used herein, means a method of delaying and/or precluding the onset, recurrence or spread, in whole or in part, of a disorder, disease or condition, or one or more of the symptoms associated with a disorder, disease, or condition, in particular, a solid tumor or hematological cancer; barring a subject from acquiring a cancer, in particular, a solid tumor or hematological cancer; or reducing a subject's risk of acquiring a cancer, in particular, a solid tumor or hematological cancer.

The term "effective amount" in connection with an amorphous form of Compound 1 means a amount capable of treating or preventing a disorder, disease or condition, or symptoms thereof, as disclosed herein. The effective amount of an amorphous form of Compound 1, for example in a pharmaceutical composition, may be at a level that will exercise the desired effect; for example, about 0.005 mg/kg of a subject's body weight to about 100 mg/kg of a patient's body weight in unit dosage for parenteral administration. As will be apparent to those skilled in the art, it is to be expected that the effective amount of an amorphous form of Compound 1 disclosed herein may vary depending on the severity of the indication being treated.

The terms "patient" and "subject" as used herein include an animal, including, but not limited to, an animal such a cow, monkey, horse, sheep, pig, chicken, turkey, quail, cat, dog, mouse, rat, rabbit or guinea pig, in one embodiment a mammal, in another embodiment a human. In one embodiment, a subject is a human having or at risk for having a solid tumor or hematological cancer, or a symptom thereof. In one embodiment, a patient is a human having histologically or cytologically-confirmed TNBC, including subjects who have progressed on (or not been able to tolerate) standard anticancer therapy or for whom no standard anticancer therapy exists.

As used herein, and unless otherwise specified, the terms "cancer" refers to or describes the physiological condition in mammals that is typically characterized by unregulated cell growth. Examples of cancer include solid tumors and hematological cancer. In some embodiments, the cancer is a primary cancer, in others, the cancer is metastasized. In one embodiment, the cancer is breast cancer. In another embodiment, the cancer is triple negative breast cancer.

"Triple negative breast cancer (TNBC)" as used herein, means breast cancer that does not express the proteins corresponding to the estrogen receptor (ER)- and progesterone receptor (PR), and that does not overexpress the human epidermal growth factor receptor 2 (Her2/neu) protein.

As used herein "solid tumors" includes, but is not limited to, bladder cancer (including, but not limited to, superficial bladder cancer), breast cancer (including, but not limited to, luminal B type, ER+, PR+ and Her2+breast cancer), central nervous system cancer (including, but not limited to, glioblastoma multiforme (GBM), glioma, medulloblastoma, and astrocytoma), colorectal cancer, gastrointestinal cancer (including, but not limited to, stomach cancer, oesophagus cancer, and rectum cancer), endocrine cancer (including, but not limited to, thyroid cancer, and adrenal gland cancer), eye cancer (including, but not limited to, retinoblastoma), female genitourinary cancer (including, but not limited to, cancer of the placenta, uterus, vulva, ovary, cervix), head and neck cancer (including, but not limited to, cancer of the pharynx, oesophagus, and tongue), liver cancer, lung cancer (including, but not limited to, non-small cell lung cancer (NSCLC), small cell lung cancer (SCLC), mucoepidermoid, bronchogenic, squamous cell carcinoma (SQCC), and analplastic/NSCLC), skin cancer (including, but not limited to, melanoma, and SQCC), soft tissue cancer (including but not limited to, sarcoma, Ewing's sarcoma, and rhabdomyosarcoma), bone cancer (including, but not limited to, sarcoma, Ewing's sarcoma, and osteosarcoma), squamous cell cancer (including, but not limited to, lung, esophageal, cervical, and head and neck cancer), pancreas cancer, kidney cancer (including, but not limited to, renal Wilm's tumor and renal cell carcinoma), and prostate cancer. In some embodiments, the solid tumor is breast cancer, colon cancer, lung cancer or bladder cancer. In one such embodiment, the solid tumor is superficial bladder cancer. In another, the solid tumor is lung squamous cell carcinoma. In yet another embodiment, the solid tumor is luminal B type breast cancer.

As used herein "hematological cancer" includes, but is not limited to, leukemia (including, but not limited to, acute lymphocytic leukemia (ALL), chronic myeloid leukemia (CML), acute T-cell leukemia, B cell precursor leukemia, acute promyelocytic leukemia (APML), plasma cell leukemia, myelomonoblastic/T-ALL, B myelomonocytic leukemia, erythroleukemia, and acute myeloid leukemia (AML)), lymphoma (including but not limited to Hodgkin's lymphoma, non-Hodgkin's lymphoma (NHL), Burkitt's lymphoma (BL), B cell lymphoma, lymphoblastic lymphoma, follicular lymphoma (FL), diffuse large B-cell lymphoma (DLBCL), large cell immunoblastic lymphoma), and multiple myeloma.

In the context of a cancer, inhibition may be assessed by inhibition of disease progression, inhibition of tumor growth, reduction of primary tumor, relief of tumor-related symptoms, inhibition of tumor secreted factors (including tumor secreted hormones, such as those that contribute to carcinoid syndrome), delayed appearance of primary or secondary tumors, slowed development of primary or secondary tumors, decreased occurrence of primary or secondary tumors, slowed or decreased severity of secondary effects of disease, arrested tumor growth and regression of tumors, increased Time To Progression (TTP), increased Progression Free Survival (PFS), increased Overall Survival (OS), among others. OS as used herein means the time from randomization until death from any cause, and is measured in the intent-to-treat population. TTP as used herein means the time from randomization until objective tumor progression; TTP does not include deaths. As used herein, PFS means the time from randomization until objective tumor progression or death. In one embodiment, PFS rates will be computed using the Kaplan-Meier estimates. In the extreme, complete inhibition, is referred to herein as prevention or chemoprevention. In this context, the term "prevention" includes either preventing the onset of clinically evident cancer altogether or preventing the onset of a preclinically evident stage of a cancer. Also intended to be encompassed by this definition is the prevention of transformation into malignant cells or to arrest or reverse the progression of premalignant cells to malignant cells. This includes prophylactic treatment of those at risk of developing a cancer.

In certain embodiments, the treatment of lymphoma may be assessed by the International Workshop Criteria (IWC) for non-Hodgkin lymphoma (NHL) (see Cheson B D, Pfistner B, Juweid, M E, et. al. Revised Response Criteria for Malignant Lymphoma. J. Clin. Oncol: 2007: (25) 579-586), using the response and endpoint definitions shown below:

| Response | Definition | Nodal Masses | Spleen, liver | Bone Marrow |
| --- | --- | --- | --- | --- |
| CR | Disappearance of all evidence of disease | (a) FDG-avid or PET positive prior to therapy; mass of any size permitted if PET negative (b) Variably FDG-avid or PET negative; regression to normal size on CT | Not palpable, nodules disappeared | Infiltrate cleared on repeat biopsy; if indeterminate by morphology, immunohistochemistry should be negative |
| PR | Regression of measurable disease and no new sites | ≥50% decrease in SPD of up to 6 largest dominant masses; no increase in size of other nodes (a) FDG-avid or PET positive prior to therapy; one or more PET positive at previously involved site (b) Variably FDG-avid or PET negative; regression on CT | ≥50% decrease in SPD of nodules (for single nodule in greatest transverse diameter); no increase in size of liver or spleen | Irrelevant if positive prior to therapy; cell type should be specified |
| SD | Failure to attain CR/PR or PD | (a) FDG-avid or PET positive prior to therapy; PET positive at prior sites of disease and no new sites on CT or PET | | |

| Response | Definition | Nodal Masses | Spleen, liver | Bone Marrow |
| --- | --- | --- | --- | --- |
| PD or relapsed disease | Any new lesion or increase by ≥50% of previously involved sites from nadir | (b) Variably FDG-avid or PET negative; no change in size of previous lesions on CT Appearance of a new lesion(s) ≥1.5 cm in any axis, ≥50% increase in SPD of more than one node, or ≥50% increase in longest diameter of a previously identifed node ≥1 cm in short axis Lesions PET positive if FDG-avid lymphoma or PET positive prior to therapy | ≥50% increase from nadir in the SPD of any previous lesions | New or recurrent involvement |

Abbreviations: CR, complete remission; FDG, [$^{18}$F]fluorodeoxyglucose; PET, positron emission tomography; CT, computed tomography; PR, partial remission; SPD, sum of the product of the diameters; SD, stable disease; PD, progressive disease.

| End point | Patients | Definition | Measured from |
| --- | --- | --- | --- |
| Primary | | | |
| Overall survival | All | Death as a result of any cause | Entry onto study |
| Progression-free survival | All | Disease progression or death as a result of any cause | Entry onto study |
| Secondary | | | |
| Event-free survival | All | Failure of treatment or death as result of any cause | Entry onto study |
| Time to progression | All | Time to progression or death as a result of lymphoma | Entry onto study |
| Disease-free survival | In CR | Time to relapse or death as a result of lymphoma or acute toxicity of treatment | Documentation of response |
| Response duration | In CR or PR | Time to relapse or progression | Documentation of response |
| Lymphoma-specific survival | All | Time to death as a result of lymphoma | Entry onto study |
| Time to next treatment | All | Time to new treatment | End of primary treatment |

Abbreviations: CR: complete remission: PR: partial remission.

In one embodiment, the end point for lymphoma is evidence of clinical benefit. Clinical benefit may reflect improvement in quality of life, or reduction in patient symptoms, transfusion requirements, frequent infections, or other parameters. Time to reappearance or progression of lymphoma-related symptoms can also be used in this end point.

In certain embodiments, the treatment of CLL may be assessed by the International Workshop Guidelines for CLL (see Hallek M, Cheson B D, Catovsky D, et al. Guidelines for the diagnosis and treatment of chronic lymphocytic leukemia: a report from the International Workshop on Chronic Lymphocytic Leukemia updating the National Cancer Institute-Working Group 1996 guidelines. Blood, 2008; (111) 12: 5446-5456) using the response and endpoint definitions shown therein and in particular:

| Parameter | CR | PR | PD |
| --- | --- | --- | --- |
| Group A | | | |
| Lymphadenopathy† | None >1.5 cm | Decrease ≥50% | Increase ≥50% |
| Hepatomegaly | None | Decrease ≥50% | Increase ≥50% |
| Splenomegaly | None | Decrease ≥50% | Increase ≥50% |
| Blood lymphocytes | <4000/μL | Decrease ≥50% from baseline | Increase ≥50% over baseline |
| Marrow‡ | Normocellular, <30% lymphocytes, no B-lymphoid nodules. Hypocellular marrow defines CRi (5.1.6). | 50% reduction in marrow infiltrate, or B-lymphoid nodules | |

-continued

| Parameter | CR | PR | PD |
|---|---|---|---|
| Group B | | | |
| Platelet count | >100000/μL | >100000/μL or increase ≥50% over baseline | Decrease of ≥50% from baseline secondary to CLL |
| Hemoglobin | >11.0 g/dL | >11 g/dL or increase ≥50% over baseline | Decrease of >2 g/dL from baseline secondary to CLL |
| Neutrophils[‡] | >1500/μL | >1500/μL or >50% improvement over baseline | |

Group A criteria define the tumor load; Group B criteria define the function of the hematopoietic system (or marrow). CR (complete remission): all of the criteria have to be met, and patients have to lack disease-related constitutional symptoms; PR (partial remission): at least two of the criteria of group A plus one of the criteria of group B have to be met; SD is absence of progressive disease (PD) and failure to achieve at least a PR; PD: at least one of the above criteria of group A or group B has to be met. Sum of the products of multiple lymph nodes (as evaluated by CT scans in clinical trials, or by physical examination in general practice). These parameters are irrelevant for some response categories.

In certain embodiments, the treatment of multiple myeloma may be assessed by the International Uniform Response Criteria for Multiple Myeloma (IURC) (see Durie B G M, Harousseau J-L, Miguel J S, et al. International uniform response criteria for multiple myeloma. Leukemia, 2006; (10) 10: 1-7), using the response and endpoint definitions shown below:

| Response Subcategory | Response Criteria[a] |
|---|---|
| sCR | CR as defined below plus<br>Normal FLC ratio and<br>Absence of clonal cells in bone marrow[b] by immunohistochemistry or immunofluorescence[c] |
| CR | Negative immunofixation on the serum and urine and<br>Disappearance of any soft tissue plasmacytomas and <5% plasma cells in bone marrow[b] |
| VGPR | Serum and urine M-protein detectable by immunofixation but not on electrophoresis or 90% or greater reduction in serum M-protein plus urine M-protein level <100 mg per 24 h |
| PR | ≥50% reduction of serum M-protein and reduction in 24-h urinary M-protein by ≥90% or to <200 mg per 24 h<br>If the serum and urine M-protein are unmeasurable,[d] a ≥50% decrease in the difference between involved and uninvolved FLC levels is required in place of the M-protein criteria<br>If serum and urine M-protein are unmeasurable, and serum free light assay is also unmeasurable, ≥50% reduction in plasma cells is required in place of M-protein, provided baseline bone marrow plasma cell percentage was ≥30%<br>In addition to the above listed criteria, if present at baseline, a ≥50% reduction in the size of soft tissue plasmacytomas is also required |
| SD (not recommended for use as an indicator of response; stability of disease is best described by providing the time to progression estimates) | Not meeting criteria for CR, VGPR, PR or progressive disease |

Abbreviations:
CR, complete response;
FLC, free light chain;
PR, partial response;
SD, stable disease;
sCR, stringent complete response;
VGPR, very good partial response;

[a]All response catagories require two consecutive assessments made at anytime before the institution of any new thearapy; all catagories also require no known evidence of progressive or new bone lesions if radiographic studies were performed. Radiographics studies are not required to satisfy these response requirements;
[b]Confirmation will repeat bone marrow biopsy not needed;
[c]Presence/absence of clonal cells is based upon the κ/λ ratio. An abnormal κ/λ ratio by immunohistochemistry and/or immunofluorescence requires a minimum of 100 plasma cells for analysis. An abnormal ratio reflecting presence of an abnormal clone is κ/λ of >4:1 or <1:2.
[d]Measurable disease defined by at least one of the following measurements: Bone marrow plasma cells ≥30%; Serum M-protein ≥1 g/dl (≥10 gm/l)[10 g/l]; Urine m-protein ≥200 mg/24 h; Serum FLC assay: Involved FLC level ≥10 mg/dl (≥100 mg/l); provided serum FLC ratio is abnormal.

In certain embodiments, the treatment of a cancer may be assessed by Response Evaluation Criteria in Solid Tumors (RECIST 1.1) (see Thereasse P., et al. New Guidelines to Evaluate the Response to Treatment in Solid Tumors. J. of the National Cancer Institute; 2000; (92) 205-216 and Eisenhauer E. A., Therasse P., Bogaerts J., et al. New response evaluation criteria in solid tumours: Revised RECIST guideline (version 1.1). European J. Cancer; 2009; (45) 228-247). Overall responses for all possible combinations of tumor responses in target and non-target lesions with our without the appearance of new lesions are as follows:

| Target lesions | Non-target lesions | New lesions | Overall response |
|---|---|---|---|
| CR | CR | No | CR |
| CR | Incomplete response/SD | No | PR |
| PR | Non-PD | No | PR |
| SD | Non-PD | No | SD |
| PD | Any | Yes or no | PD |
| Any | PD | Yes or no | PD |
| Any | Any | Yes | PD |

CR = complete response; PR = partial response; SD = stable disease; and PD = progressive disease.

With respect to the evaluation of target lesions, complete response (CR) is the disappearance of all target lesions, partial response (PR) is at least a 30% decrease in the sum of the longest diameter of target lesions, taking as reference the baseline sum longest diameter, progressive disease (PD) is at least a 20% increase in the sum of the longest diameter of target lesions, taking as reference the smallest sum longest diameter recorded since the treatment started or the appearance of one or more new lesions and stable disease (SD) is neither sufficient shrinkage to qualify for partial response nor sufficient increase to qualify for progressive disease, taking as reference the smallest sum longest diameter since the treatment started.

With respect to the evaluation of non-target lesions, complete response (CR) is the disappearance of all non-target lesions and normalization of tumor marker level; incomplete response/stable disease (SD) is the persistence of one or more non-target lesion(s) and/or the maintenance of tumor marker level above the normal limits, and progressive disease (PD) is the appearance of one or more new lesions and/or unequivocal progression of existing non-target lesions.

The procedures, conventions, and definitions described below provide guidance for implementing the recommendations from the Response Assessment for Neuro-Oncology (RANO) Working Group regarding response criteria for high-grade gliomas (Wen P., Macdonald, D R., Reardon, D A., et al. Updated response assessment criteria for highgrade gliomas: Response assessment in neuro-oncology working group. J Clin Oncol 2010; 28: 1963-1972). Primary modifications to the RANO criteria for Criteria for Time Point Responses (TPR) can include the addition of operational conventions for defining changes in glucocorticoid dose, and the removal of subjects' clinical deterioration component to focus on objective radiologic assessments. The baseline MRI scan is defined as the assessment performed at the end of the post-surgery rest period, prior to re-initiating compound treatment. The baseline MRI is used as the reference for assessing complete response (CR) and partial response (PR). Whereas, the smallest SPD (sum of the products of perpendicular diameters) obtained either at baseline or at subsequent assessments will be designated the nadir assessment and utilized as the reference for determining progression. For the 5 days preceding any protocol-defined MRI scan, subjects receive either no glucocorticoids or are on a stable dose of glucocorticoids. A stable dose is defined as the same daily dose for the 5 consecutive days preceding the MRI scan. If the prescribed glucocorticoid dose is changed in the 5 days before the baseline scan, a new baseline scan is required with glucocorticoid use meeting the criteria described above. The following definitions will be used.

Measurable Lesions: Measurable lesions are contrast-enhancing lesions that can be measured bidimensionally. A measurement is made of the maximal enhancing tumor diameter (also known as the longest diameter, LD). The greatest perpendicular diameter is measured on the same image. The cross hairs of bidimensional measurements should cross and the product of these diameters will be calculated.

Minimal Diameter: T1-weighted image in which the sections are 5 mm with 1 mm skip. The minimal LD of a measurable lesion is set as 5 mm by 5 mm. Larger diameters may be required for inclusion and/or designation as target lesions. After baseline, target lesions that become smaller than the minimum requirement for measurement or become no longer amenable to bidimensional measurement will be recorded at the default value of 5 mm for each diameter below 5 mm. Lesions that disappear will be recorded as 0 mm by 0 mm.

Multicentric Lesions: Lesions that are considered multicentric (as opposed to continuous) are lesions where there is normal intervening brain tissue between the two (or more) lesions. For multicentric lesions that are discrete foci of enhancement, the approach is to separately measure each enhancing lesion that meets the inclusion criteria. If there is no normal brain tissue between two (or more) lesions, they will be considered the same lesion.

Nonmeasurable Lesions: All lesions that do not meet the criteria for measurable disease as defined above will be considered non-measurable lesions, as well as all nonenhancing and other truly nonmeasurable lesions. Nonmeasurable lesions include foci of enhancement that are less than the specified smallest diameter (i.e., less than 5 mm by 5 mm), nonenhancing lesions (e.g., as seen on T1-weighted post-contrast, T2-weighted, or fluid-attenuated inversion recovery (FLAIR) images), hemorrhagic or predominantly cystic or necrotic lesions, and leptomeningeal tumor. Hemorrhagic lesions often have intrinsic T1-weighted hyperintensity that could be misinterpreted as enhancing tumor, and for this reason, the pre-contrast T1-weighted image may be examined to exclude baseline or interval sub-acute hemorrhage.

At baseline, lesions will be classified as follows: Target lesions: Up to 5 measurable lesions can be selected as target lesions with each measuring at least 10 mm by 5 mm, representative of the subject's disease; Non-target lesions: All other lesions, including all nonmeasurable lesions (including mass effects and T2/FLAIR findings) and any measurable lesion not selected as a target lesion. At baseline, target lesions are to be measured as described in the definition for measurable lesions and the SPD of all target lesions is to be determined. The presence of all other lesions is to be documented. At all post-treatment evaluations, the baseline classification of lesions as target and non-target lesions will be maintained and lesions will be documented and described in a consistent fashion over time (e.g., recorded in the same order on source documents and eCRFs). All measurable and nonmeasurable lesions must be assessed using the same technique as at baseline (e.g., subjects should be imaged on the same MRI scanner or at least with the same magnet strength) for the duration of the study to reduce difficulties in interpreting changes. At each evaluation, target lesions will be measured and the SPD calculated. Non-target lesions will be assessed qualitatively and new lesions, if any, will be documented separately. At each evaluation, a time point response will be determined for target lesions, non-target lesions, and new lesion. Tumor progression can be established even if only a subset of lesions is assessed. However, unless progression is observed, objective status (stable disease, PR or CR) can only be determined when all lesions are assessed.

Confirmation assessments for overall time point responses of CR and PR will be performed at the next scheduled assessment, but confirmation may not occur if scans have an interval of <28 days. Best response, incorporating confirmation requirements, will be derived from the series of time points.

5.2 Compound 1

The amorphous form, formulations and methods of use provided herein relate to Compound 1:

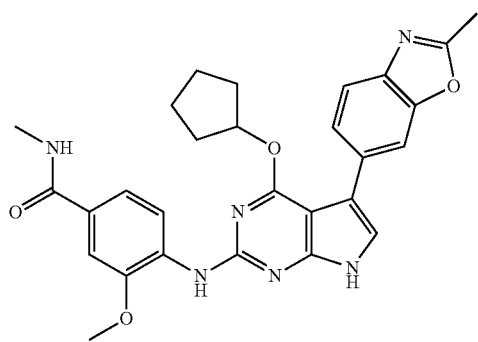

having the name 4-((4-(Cyclopentyloxy)-5-(2-methyl-benzo[d]oxazol-6-yl)-7H-pyrrolo[2,3-d]pyrimidin-2-yl) amino)-3-methoxy-N-methylbenzamide, including tautomers thereof.

Compound 1 can be prepared using reagents and methods known in the art, including the methods provided in U.S. patent application Ser. No. 14/155,485, filed on Jan. 15, 2014, the entire content of which is incorporated herein by reference.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

5.3 Solid Forms of Compound 1

Solid forms of Compound 1 may be characterized using a number of methods known to a person skilled in the art, including, but not limited to, X-ray powder diffraction (XRPD), microscopy (e.g., scanning electron microscopy (SEM)) and thermal analysis (e.g., differential scanning calorimetry (DSC). The particle size and size distribution of the solid form provided herein may be determined by conventional methods, such as laser light scattering technique.

It should be understood that the numerical values of the peaks of an X-ray powder diffraction pattern may vary slightly from one machine to another or from one sample to another, and so the values quoted are not to be construed as absolute, but with an allowable variability, such as ±0.2°2θ (see United State Pharmacopoeia, page 2228 (2003)).

5.3.1 Amorphous Form

In certain embodiments, provided herein is an amorphous form of Compound 1. In one embodiment, the amorphous form is an anhydrous solid form of Compound 1.

In one embodiment, the amorphous form has an X-ray powder diffraction pattern substantially as shown in FIG. 1. In one embodiment, the amorphous form has one characteristic X-ray halo as depicted in FIG. 1.

Figure 2A:
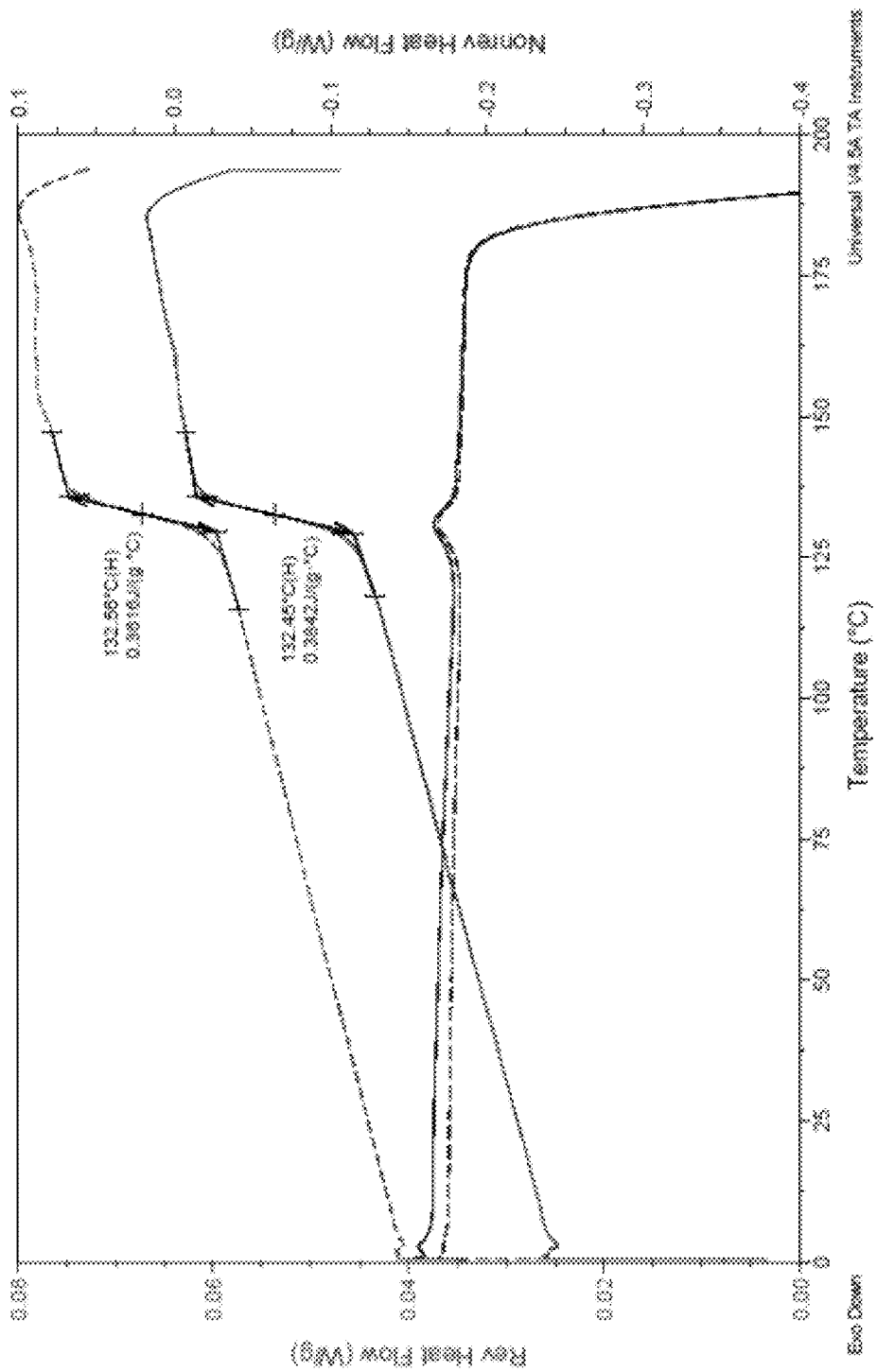
FIG. 2A and FIG. 2B depict representative DSC thermograms of amorphous Compound 1.
Figure 2B:
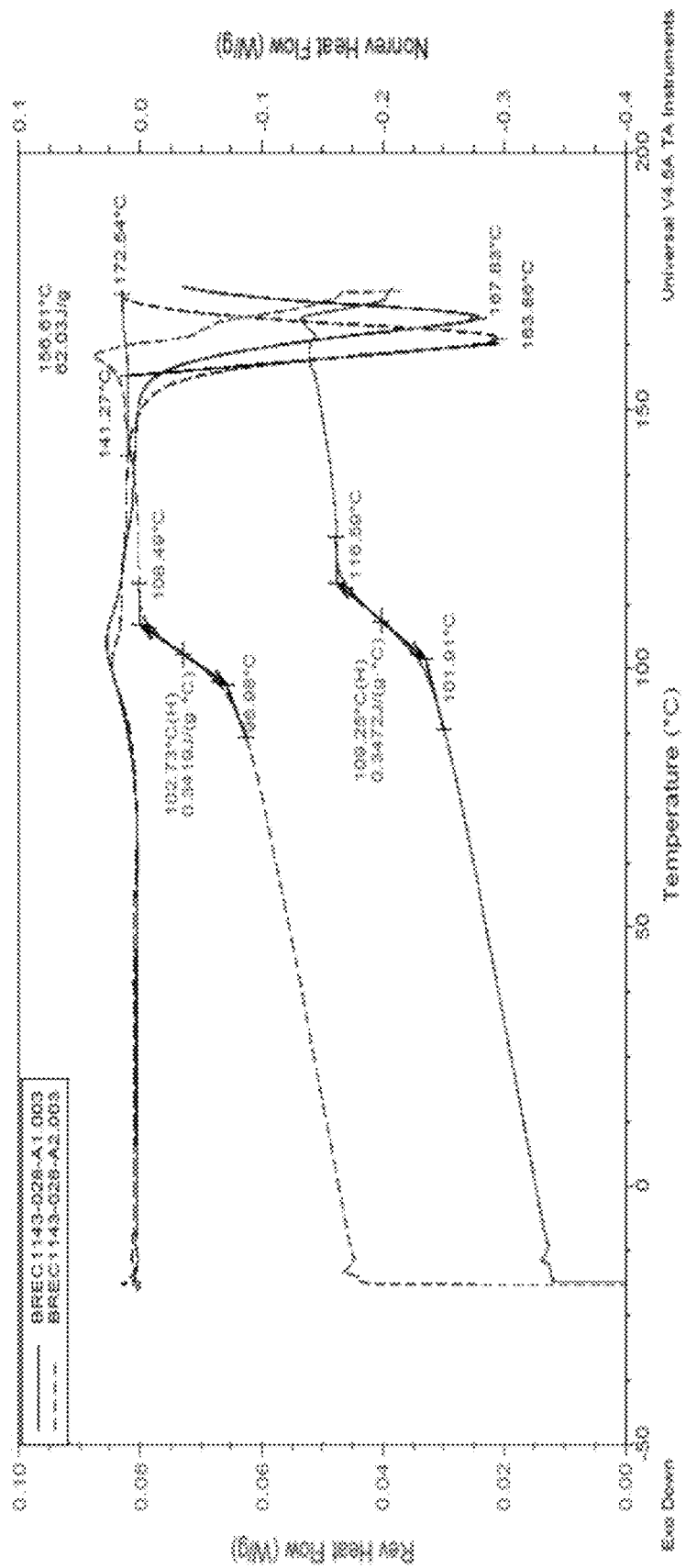

In one embodiment, provided herein is an amorphous form of Compound 1 having a DSC thermogram substantially as depicted in FIG. 2A or FIG. 2B. In one embodiment, the DSC thermogram comprising a glass transition or melting event between about 100° C. to about 135° C. In one embodiment, the DSC thermogram comprises a glass transition or melting event between about 125° C. to about 135° C. (for example, about 132.5° C. as in FIG. 2A) when heated from approximately 0° C. to approximately 200° C. In another embodiment, the DSC thermogram comprises a glass transition or melting event between about 100° C. to about 110° C. (for example, about 106° C. as in FIG. 2B) when heated from approximately -25° C. to approximately 200° C. In one embodiment, the DSC thermogram comprises an exotherm between about 163° C. and about 168° C., for example at about 163° C. or at about 168° C. Without being limited by theory, it is believed that due to the relatively high glass event and/or melting temperature of the amorphous form of Compound 1, the amorphous form of Compound 1 is stable, such that it does not readily convert to a crystalline form.

Figure 3A:
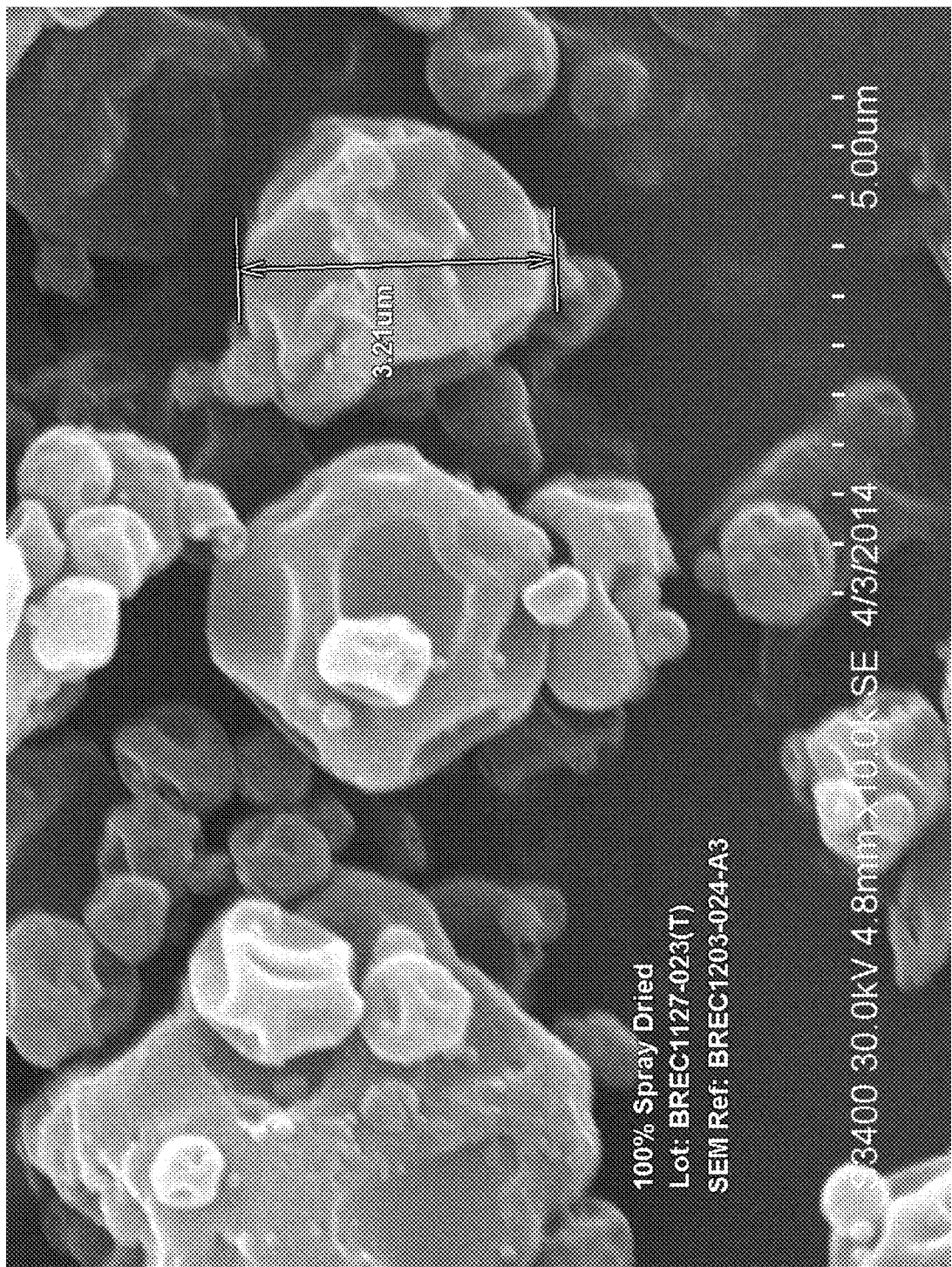
FIG. 3A and FIG. 3B depict representative SEM images of amorphous Compound 1.
Figure 3B:
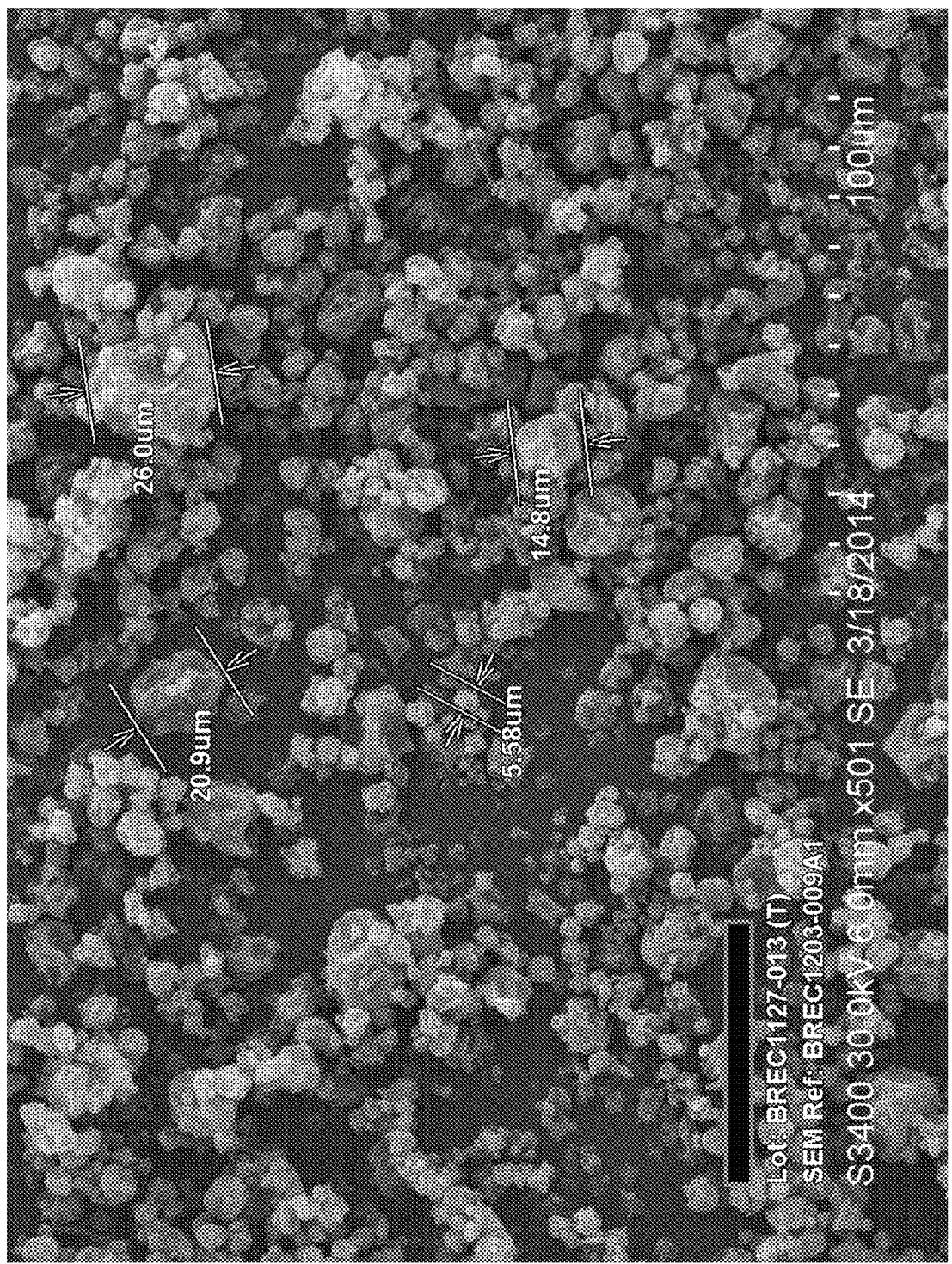

In one embodiment, the amorphous form has a SEM digital image substantially as shown in FIG. 3A or FIG. 3B.

Figure 4A:
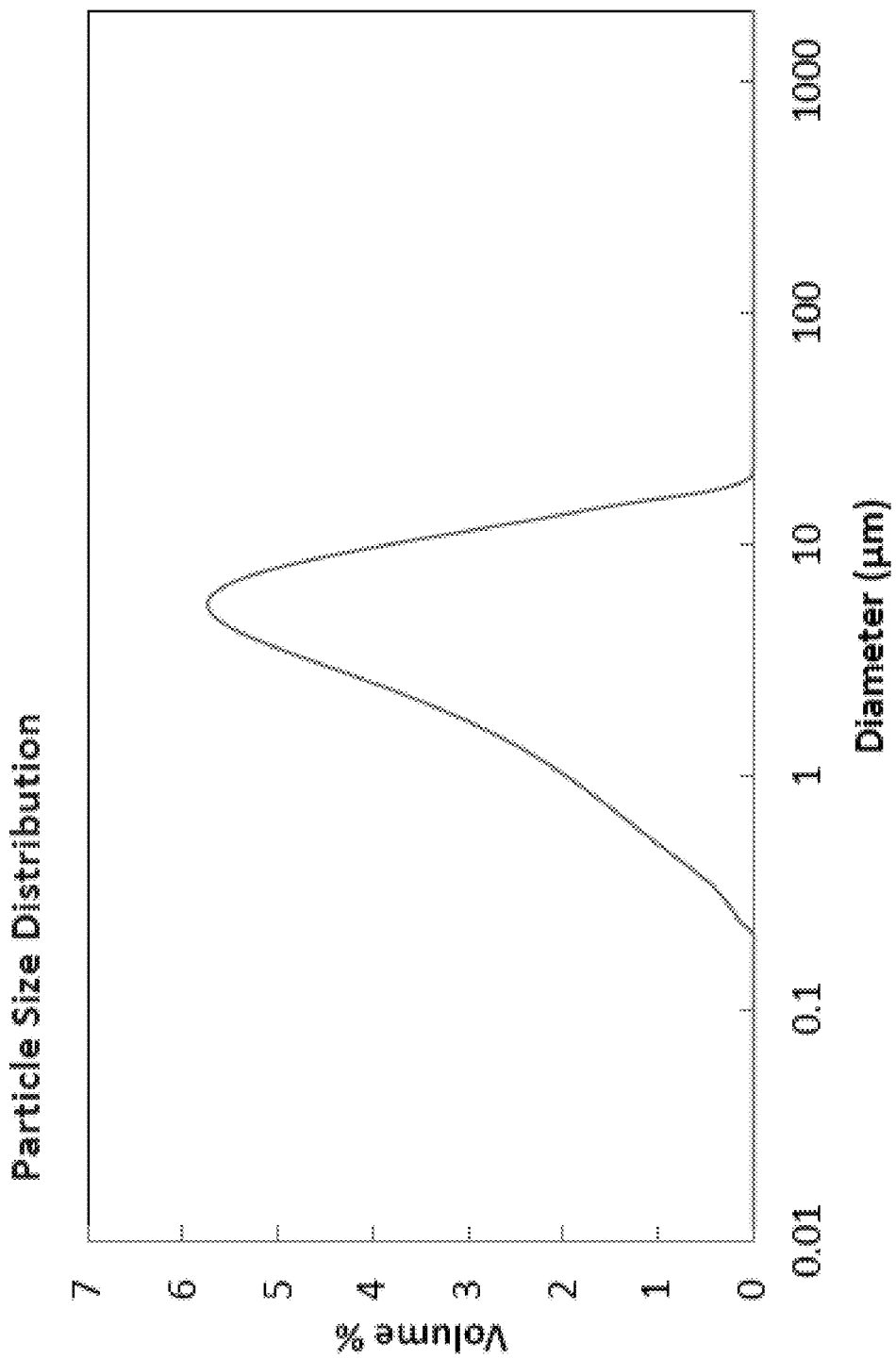
FIG. 4A, FIG. 4B and FIG. 4C depict representative particle size distributions of amorphous Compound 1.
Figure 4B:
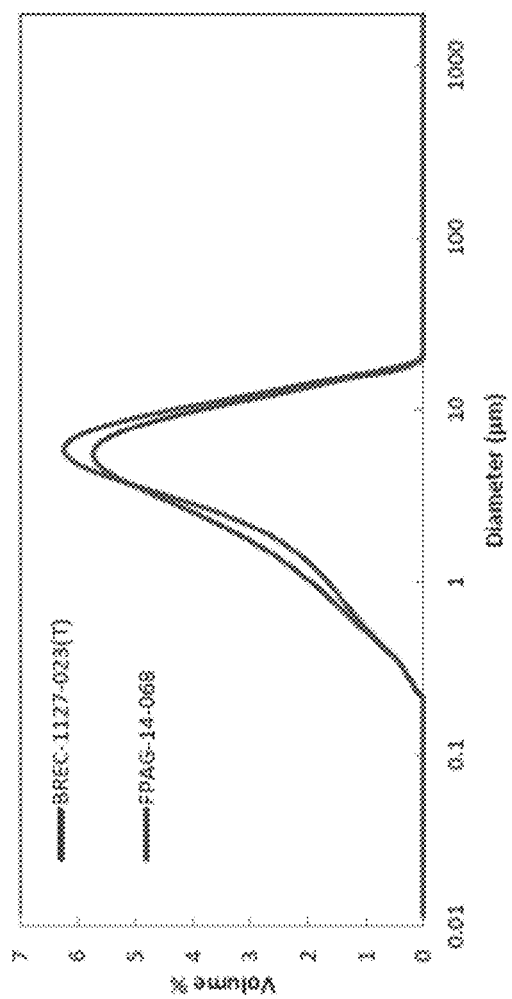
Figure 4C:
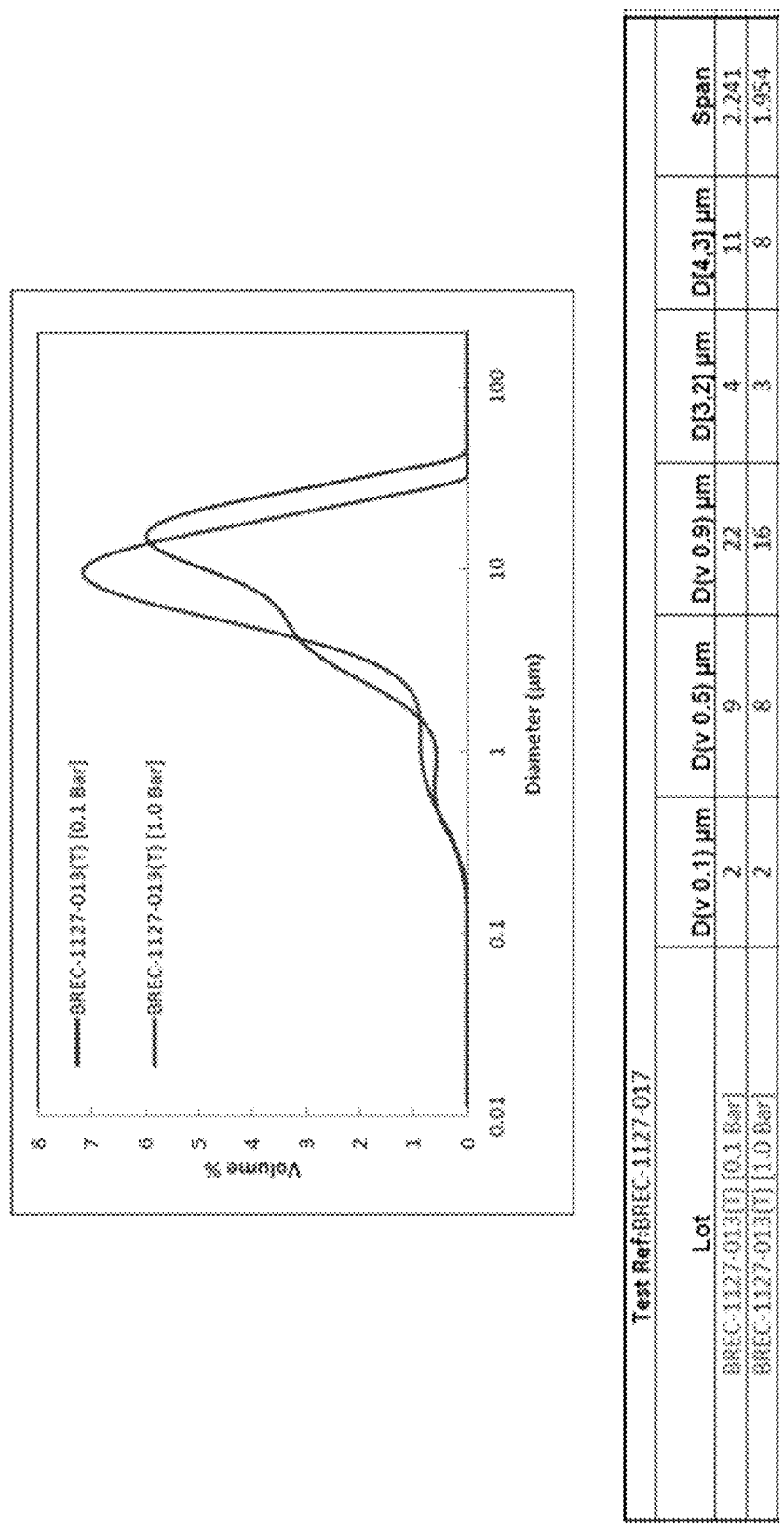

In one embodiment, the amorphous form has a particle size distribution pattern substantially as shown in FIG. 4A, FIG. 4B or FIG. 4C. In some embodiments, the amorphous form has a particle size distribution between about 0.1 μm and about 60 μm. In some embodiments, the amorphous form has a particle size distribution between about 0.2 μm and about 30 μm. In still others, the amorphous form has a particle size distribution between about 0.1 μm and about 0.5 μm. In some embodiments, the amorphous form has a particle size distribution with 90% of the particles having an average diameter of about 10 μm. In some embodiments, the amorphous form has a particle size below about 10 μm. In some embodiments, the amorphous form has a particle size distribution with 90% of the particles having an average diameter of about 16 μm. In some embodiments, the amorphous form has a particle size below about 16 μm. In still other embodiments, the amorphous form has a particle size distribution with 90% of the particles having an average diameter of about 22 μm. In some embodiments, the amorphous form has a particle size belowabout 22 μm.

Figure 6:
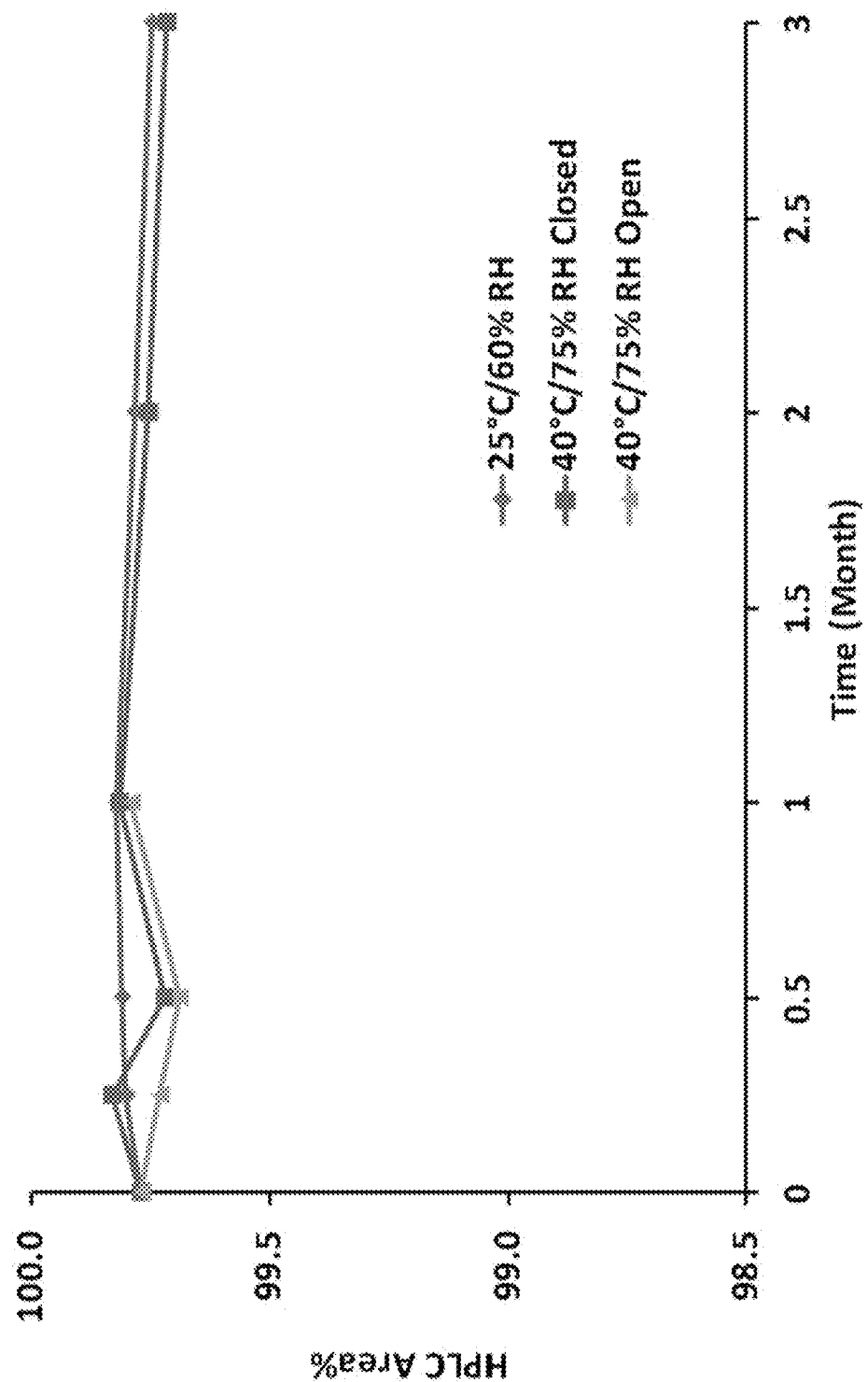
FIG. 6 depicts a stability study of the amorphous form based on its HPLC purity over 3 months.

In one embodiment, the amorphous form has no significant changes in its HPLC purity over 3 months substantially as shown in FIG. 6. In some such embodiments, the change in HPLC purity is less than about 0.5% decrease in HPLC purity over 3 months. In others, the change in HPLC purity is less than about 0.25% or less than about 0.3% decrease in HPLC purity over 3 months.

Figure 7:
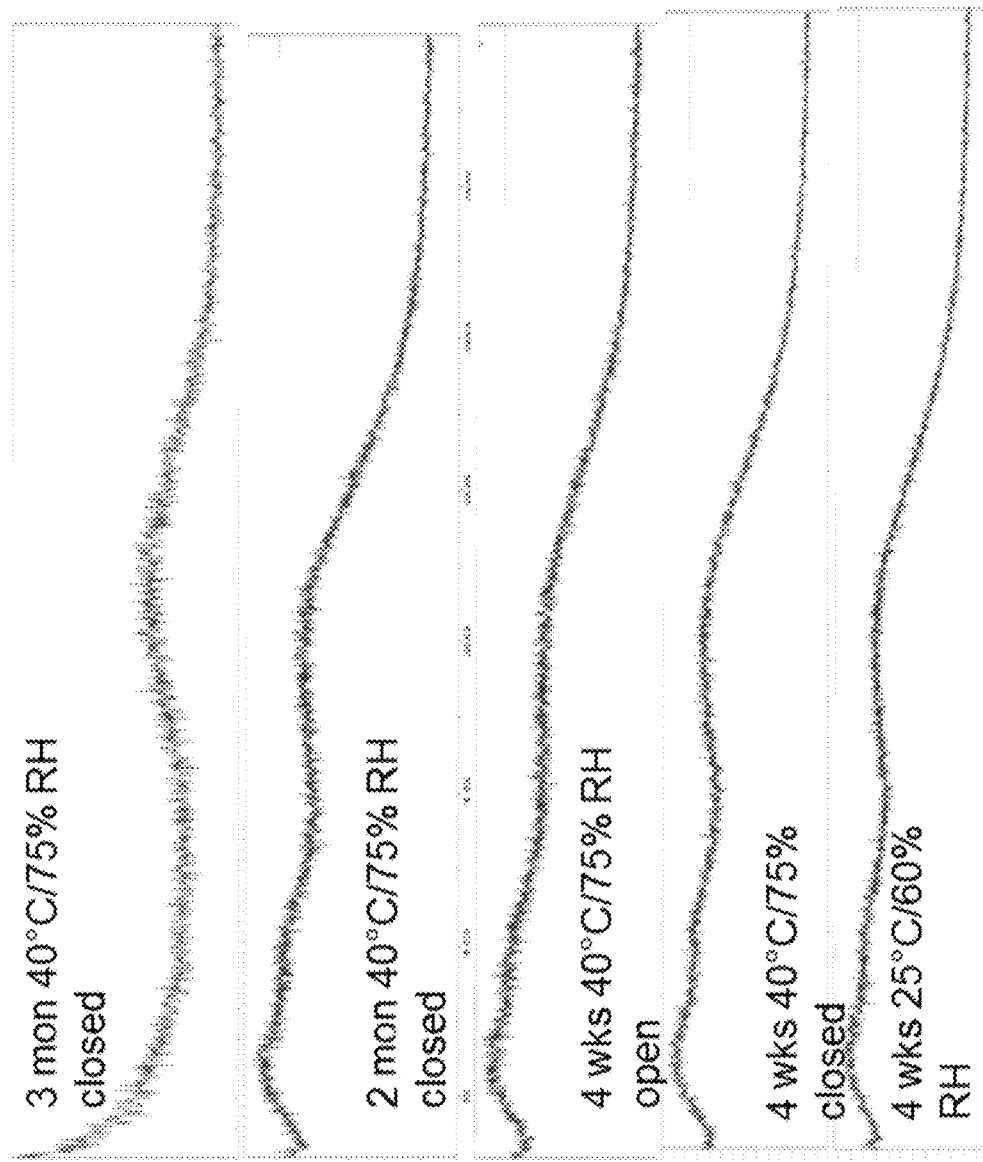
FIG. 7 depicts a stability study of the amorphous form based on its XRPD over 3 months.

In one embodiment, the amorphous form has no significant changes in its XRPD over 3 months substantially as shown in FIG. 7.

In still another embodiment, the amorphous form is substantially pure. In certain embodiments, the substantially pure amorphous form is substantially free of other solid forms. In certain embodiments, the purity of the substantially pure amorphous form is no less than about 95%, no less than about 96%, no less than about 97%, no less than about 98%, no less than about 98.5%, no less than about 99%, no less than about 99.5%, or no less than about 99.8%. In certain embodiments, the amorphous form of Compound 1 provided herein is substantially non-crystalline. In certain embodiments, the amorphous form of Compound 1 provided herein is non-crystalline. In certain embodiments, the amorphous form of Compound 1 provided herein is non-crystalline as determined by X-ray diffraction.

5.4 Methods of Manufacture

Figure 5:
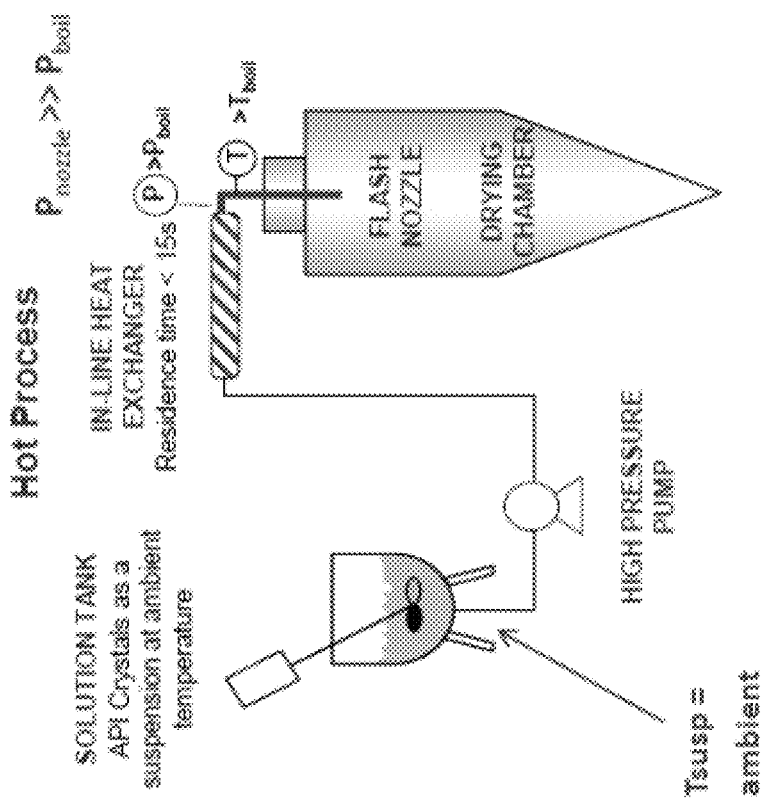
FIG. 5 depicts a representative preparation process of the amorphous form.

In certain embodiments, the amorphous form provided herein can be obtained by a spray-drying process of Compound 1 substantially as shown in FIG. 5. In certain embodiments, the spray-drying process comprises 1) mixing Compound 1 with a solvent (e.g., methanol); 2) heating the mixture to a certain temperature (e.g., about 110-130° C. or about 121° C.); 3) spray-drying the mixture; and 4) collecting resulting solids. In certain embodiments, the spray-drying process comprises 1) mixing Compound 1 with methanol; 2) heating the mixture to about 121° C.; 3) spray-drying the mixture; and 4) collecting resulting solids. In another embodiment, the spray-drying process comprises 1) mixing of Compound 1 in acetone; 2) spray-drying the solution and 3) collecting resulting solids. Without being limited by theory, while the amorphous form of Compound 1 was obtained using spray-drying techniques provided herein, standard evaporation methods did not provide the amorphous form of Compound 1.

5.5 Methods of Use

The amorphous form of Compound 1 has utility as a pharmaceutical to treat, prevent or improve cancer in animals or humans. Accordingly, provided herein are uses of the amorphous form of Compound 1, including the treatment or prevention of those cancers set forth herein. The methods provided herein comprise the administration of an effective amount of the amorphous form of Compound 1 to a subject in need thereof.

In another aspect provided herein are methods for treating or preventing a cancer, comprising administering to a subject in need thereof an effective amount of the amorphous form of Compound 1, as described herein. In some embodiments, the cancer is a solid tumor or a hematological tumor. In some embodiments, the cancer is triple negative breast cancer (TNBC). In another aspect, provided herein is the amorphous form of Compound 1 for use in methods for treating or preventing cancer.

In some embodiments, the solid tumor is bladder cancer (including superficial bladder cancer), breast cancer (including luminal B type, ER+, PR+ and Her2+breast cancer), central nervous system cancer (including glioblastoma multiforme (GBM), glioma, medulloblastoma, and astrocytoma), colorectal cancer, gastrointestinal cancer (including stomach cancer, oesophagus cancer, and rectum cancer), endocrine cancer (including thyroid cancer, and adrenal gland cancer), eye cancer (including retinoblastoma), female genitourinary cancer (including cancer of the placenta, uterus, vulva, ovary, cervix), head and neck cancer (including cancer of the pharynx, oesophagus, and tongue), liver cancer, lung cancer (including non-small cell lung cancer (NSCLC), small cell lung cancer (SCLC), mucoepidermoid, bronchogenic, squamous cell carcinoma (SQCC), and anaplastic/NSCLC), skin cancer (including melanoma, and SQCC), soft tissue cancer (including sarcoma, Ewing's sarcoma, and rhabdomyosarcoma), bone cancer (including sarcoma, Ewing's sarcoma, and osteosarcoma), squamous cell cancer (including lung, esophageal, cervical, and head and neck cancer), pancreas cancer, kidney cancer (including renal Wilm's tumor and renal cell carcinoma), or prostate cancer. In some embodiments, the solid tumor is triple negative breast cancer. In some embodiments, the solid tumor is breast cancer, colon cancer, lung cancer or bladder cancer. In one such embodiment, the solid tumor is superficial bladder cancer. In another, the solid tumor is lung squamous cell carcinoma. In yet another embodiment, the solid tumor is luminal B type breast cancer.

In some embodiments, the hematological cancer is leukemia (including acute lymphocytic leukemia (ALL), chronic myeloid leukemia (CML), acute T-cell leukemia, B cell precursor leukemia, acute promyelocytic leukemia (APML), plasma cell leukemia, myelomonoblastic/T-ALL, B myelomonocytic leukemia, erythroleukemia, and acute myeloid leukemia (AML)), lymphoma (including Hodgkin's lymphoma, non-Hodgkin's lymphoma (NHL), Burkitt's lymphoma (BL), B cell lymphoma, lymphoblastic lymphoma, follicular lymphoma (FL), diffuse large B-cell lymphoma (DLBCL), and large cell immunoblastic lymphoma). In some embodiments the cancer is multiple myeloma.

In some embodiments, provided herein are methods for preventing cancer metastasis, comprising administering to a subject in need thereof an effective amount of an amorphous form of Compound 1, as described herein. In some embodiments, the cancer is a metastatic cancer, in particular, a metastatic solid tumor or metastatic hematologic cancer, wherein the solid tumor and hematologic cancer is as described herein. In other embodiments, provided herein are methods of preventing cancer metastasis, comprising administering to a subject in need thereof an effective amount of an amorphous form of Compound 1, as described herein. In yet another aspect, provided herein are methods of eradicating cancer stem cells in a subject, comprising administering to a subject in need thereof an effective amount of an amorphous form of Compound 1, as described herein. In other embodiments, provided herein are methods of inducing differentiation in cancer stem cells in a subject, comprising administering to a subject in need thereof an effective amount of an amorphous form of Compound 1, as described herein. In other embodiments, provided herein are methods of inducing cancer stem cell death in a subject, comprising administering to a subject in need thereof an effective amount of an amorphous form of Compound 1, as described herein. In some such embodiments, the cancer is a solid tumor, for example a CNS cancer (e.g. GBM) or breast cancer, or a hematological cancer, such as leukemia. In some embodiments, provided herein is the amorphous form of Compound 1 for use in methods for preventing cancer metastasis.

In one embodiment, provided herein are methods for achieving a Response Evaluation Criteria in Solid Tumors (RECIST 1.1) of complete response, partial response or stable disease in a patient comprising administering an effective amount of an amorphous form of Compound 1 to a patient having a cancer, in particular a solid tumor as described herein. In another embodiment, provided herein are methods to increase Progression Free Survival rates, as determined by Kaplan-Meier estimates. In one embodiment, provided herein is the amorphous form of Compound 1 for use in methods for achieving a Response Evaluation Criteria in Solid Tumors (RECIST 1.1) of complete response, partial response or stable disease in a patient.

In one embodiment, provided herein are methods for preventing or delaying a Response Evaluation Criteria in Solid Tumors (RECIST 1.1) of progressive disease in a patient, comprising administering an effective amount of an amorphous form of Compound 1 to a patient having a solid tumor as described herein. In one embodiment the prevention or delaying of progressive disease is characterized or achieved by a change in overall size of the target lesions, of for example, between −30% and +20% compared to pre-treatment. In another embodiment, the change in size of the target lesions is a reduction in overall size of more than 30%, for example, more than 50% reduction in target lesion size compared to pre-treatment. In another, the prevention is characterized or achieved by a reduction in size or a delay in progression of non-target lesions compared to pre-treatment. In one embodiment, the prevention is achieved or characterized by a reduction in the number of target lesions compared to pre-treatment. In another, the prevention is achieved or characterized by a reduction in the number or quality of non-target lesions compared to pre-treatment. In one embodiment, the prevention is achieved or characterized by the absence or the disappearance of target lesions compared to pre-treatment. In another, the prevention is achieved or characterized by the absence or the disappearance of non-target lesions compared to pre-treatment. In another embodiment, the prevention is achieved or characterized by the prevention of new lesions compared to pre-treatment. In yet another embodiment, the prevention is achieved or characterized by the prevention of clinical signs or symptoms of disease progression compared to pre-treatment, such as cancer-related cachexia or increased pain. In one embodiment, provided herein is the amorphous form of Compound 1 for use in methods for preventing or delaying a Response Evaluation Criteria in Solid Tumors (RECIST 1.1) of progressive disease in a patient.

In certain embodiments, provided herein are methods for decreasing the size of target lesions in a patient compared to pre-treatment, comprising administering an effective amount of an amorphous form of Compound 1 to a patient having a cancer, in particular a solid tumor as described herein. In certain embodiments, provided herein is an amorphous form of Compound 1 for use in the methods for decreasing the size of target lesions in a patient compared to pre-treatment.

In certain embodiments, provided herein are methods for decreasing the size of a non-target lesion in a patient compared to pre-treatment, comprising administering an effective amount of an amorphous form of Compound 1 to a patient having a cancer, in particular a solid tumor as described herein. In certain embodiments, provided herein is an amorphous form of Compound 1 for use in methods for decreasing the size of a non-target lesion in a patient compared to pre-treatment.

In certain embodiments, provided herein are methods for achieving a reduction in the number of target lesions in a patient compared to pre-treatment, comprising administering an effective amount of an amorphous form of Compound 1 to a patient having a cancer, in particular a solid tumor as described herein. In certain embodiments, provided herein is an amorphous form of Compound 1 for use in methods for achieving a reduction in the number of target lesions in a patient compared to pre-treatment.

In certain embodiments, provided herein are methods for achieving a reduction in the number of non-target lesions in a patient compared to pre-treatment, comprising administering an effective amount of an amorphous form of Compound 1 to a patient having a cancer, in particular a solid tumor as described herein. In certain embodiments, provided herein is an amorphous form of Compound 1 for use in a method for achieving a reduction in the number of non-target lesions in a patient compared to pre-treatment.

In certain embodiments, provided herein are methods for achieving an absence of all target lesions in a patient, comprising administering an effective amount of an amorphous form of Compound 1 to a patient having a cancer, in particular a solid tumor as described herein. In certain embodiments, provided herein is an amorphous form of Compound 1 for use in methods for achieving an absence of all target lesions in a patient.

In certain embodiments, provided herein are methods for achieving an absence of all non-target lesions in a patient, comprising administering an effective amount of an amorphous form of Compound 1 to a patient having a cancer, in particular a solid tumor as described herein. In certain embodiments, provided herein is an amorphous form of Compound 1 for use in methods for achieving an absence of all non-target lesions in a patient.

In certain embodiments, provided herein are methods for treating a cancer, in particular a solid tumor as described herein, the methods comprising administering an effective amount of an amorphous form of Compound 1 to a patient having a cancer, in particular a solid tumor, wherein the treatment results in a complete response, partial response or stable disease, as determined by Response Evaluation Criteria in Solid Tumors (RECIST 1.1). In certain embodiments, provided herein is an amorphous form of Compound 1 for use in methods for treating a cancer, in particular a solid tumor as described herein.

In certain embodiments, provided herein are methods for treating a cancer, in particular a solid tumor as described herein, the methods comprising administering an effective amount of an amorphous form of Compound 1 to a patient having a cancer, in particular a solid tumor as described herein, wherein the treatment results in a reduction in target lesion size, a reduction in non-target lesion size and/or the absence of new target and/or non-target lesions, compared to pre-treatment. In certain embodiments, provided herein is an amorphous form of Compound 1 for use in methods for treating a cancer, in particular a solid tumor as described herein.

In certain embodiments, provided herein are methods for treating a cancer, in particular a solid tumor as described herein, the methods comprising administering an effective amount of an amorphous form of Compound 1 to a patient having a cancer, in particular a solid tumor as described herein, wherein the treatment results in prevention or retarding of clinical progression, such as cancer-related cachexia or increased pain. In certain embodiments, provided herein is an amorphous form of Compound 1 for use in methods for treating a cancer, in particular a solid tumor as described herein.

In another embodiment, provided herein are methods for inducing a therapeutic response characterized with the International Workshop Criteria (IWC) for NHL (see Cheson B D, Pfistner B, Juweid, M E, et. al. Revised Response Criteria for Malignant Lymphoma. J. Clin. Oncol: 2007: (25) 579-586) of a patient, comprising administering an effective amount of an amorphous form of Compound 1 to a patient having a cancer, in particular hematological cancers such as lymphoma, as described herein. In another embodiment, provided herein are methods for achieving complete remission, partial remission or stable disease, as determined by the International Workshop Criteria (IWC) for NHL in a patient, comprising administering an effective amount of an amorphous form of Compound 1 to a patient having a cancer, in particular hematological cancers such as lymphoma, as described herein. In another embodiment, provided herein are methods for achieving an increase in overall survival, progression-free survival, event-free survival, time to progression, disease-free survival or lymphoma-free survival as determined by the International Workshop Criteria (IWC) for NHL in a patient, comprising administering an effective amount of an amorphous form of Compound 1 to a patient having a cancer, in particular hematological cancers such as lymphoma, as described herein. In another embodiment, provided herein is an amorphous form of Compound 1 for use in methods for inducing a therapeutic response characterized with the International Workshop Criteria (IWC) for NHL of a patient.

In another embodiment, provided herein are methods for inducing a therapeutic response assessed with the International Uniform Response Criteria for Multiple Myeloma (IURC) (see Durie B G M, Harousseau J-L, Miguel J S, et al. International uniform response criteria for multiple myeloma. Leukemia, 2006; (10) 10: 1-7) of a patient, comprising administering an effective amount of an amorphous form of Compound 1 to a patient having a cancer, in particular multiple myeloma. In another embodiment, provided herein are methods for achieving a stringent complete response, complete response, or very good partial response, as determined by the International Uniform Response Criteria for Multiple Myeloma (IURC) in a patient, comprising administering an effective amount of an amorphous form of Compound 1 to a patient having a cancer, in particular multiple myeloma. In another embodiment, provided herein are methods for achieving an increase in overall survival, progression-free survival, event-free survival, time to progression, or disease-free survival in a patient, comprising administering an effective amount of an amorphous form of Compound 1 to a patient having a cancer, in particular multiple myeloma. In another embodiment, provided herein is an amorphous form of Compound 1 for use in methods for inducing a therapeutic response assessed with the International Uniform Response Criteria for Multiple Myeloma (IURC) of a patient.

In another embodiment, provided herein are methods for inducing a therapeutic response assessed with the Response Assessment for Neuro-Oncology (RANO) Working Group for GBM (see Wen P., Macdonald, D R., Reardon, D A., et al. Updated response assessment criteria for highgrade gliomas: Response assessment in neuro-oncology working group. J. Clin. Oncol. 2010; 28: 1963-1972) of a patient, comprising administering an effective amount of an amorphous form of Compound 1 to a patient having a cancer, in particular glioblastoma multiforme (GBM). In one embodiment, RANO will be used to establish the proportion of subjects progression-free at 6 months from Day 1 relative to efficacy evaluable subjects in the GBM type. In another embodiment, provided herein is an amorphous form of Compound 1 for use in methods for inducing a therapeutic response assessed with the Response Assessment for Neuro-Oncology (RANO) Working Group for GBM of a patient.

In another embodiment, provided herein are methods for improving the Eastern Cooperative Oncology Group Performance Status (ECOG) of a patient, comprising administering an effective amount of an amorphous form of Compound 1 to a patient having a cancer, in particular a solid tumor or hematological cancer as described herein. In another embodiment, provided herein is an amorphous form of Compound 1 for use in methods for improving the Eastern Cooperative Oncology Group Performance Status (ECOG) of a patient.

In another embodiment, provided herein are methods for inducing a therapeutic response assessed by Positron Emission Tomography (PET) outcome of a patient, comprising administering an effective amount of an amorphous form of Compound 1 to a patient having a cancer, in particular a solid tumor or hematological cancer as described herein. In certain embodiments, provided herein are methods for treating a cancer, in particular a solid tumor or hematological cancer as described herein, the methods comprising administering an effective amount of an amorphous form of Compound 1 to a patient having a cancer, in particular a solid tumor or hematological cancer as described herein, wherein the treatment results in a reduction in tumor metabolic activity, for example, as measured by PET imaging. In another embodiment, provided herein is an amorphous form of Compound 1 for use in methods for inducing a therapeutic response assessed by Positron Emission Tomography (PET) outcome of a patient.

Further provided herein are methods for treating patients who have been previously treated for a cancer, in particular a solid tumor or a hematological cancer as described herein, as well as those who have not previously been treated. Because patients with a cancer have heterogenous clinical manifestations and varying clinical outcomes, the treatment given to a patient may vary, depending on his/her prognosis. The skilled clinician will be able to readily determine without undue experimentation specific secondary agents, types of surgery, and types of non-drug based standard therapy that can be effectively used to treat an individual patient with a cancer. Further provided herein is an amorphous form of Compound 1 for use in methods for treating patients who have been previously treated for a cancer, in particular a solid tumor or a hematological cancer as described herein, as well as those who have not previously been treated.

5.6 Pharmaceutical Compositions and Routes of Administration

The amorphous form of Compound 1 can be administered to a subject parenterally in the conventional form of preparations, such as injections, suspensions, solutions and emulsions. Vehicles that can be useful, either alone or in combination, to provide intravenous formulations of the amorphous form of Compound 1 include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate. An intravenous formulation can be prepared by reconstituting the amorphous form of Compound 1 with such a suitable liquid vehicle. A desired concentration of the intravenous formulation can be obtained by reconstituting an appropriate amount of the amorphous form of Compound 1 with an appropriate volume of liquid vehicle. A desired concentration of the intravenous formulation provides a therapeutically effective amount of Compound 1 to the patient in need of the intravenous formulation and maintains a therapeutically effective level of Compound 1 in the patient. The dose which is therapeutically effective will depend on the rate at which the intravenous formulation is delivered to the patient and the concentration of the intravenous formulation.

The effective amount of the amorphous form of Compound 1 in the pharmaceutical composition may be at a level that will exercise the desired effect; for example, about 0.005 mg/kg of a subject's body weight to about 100 mg/kg of a subject's body weight in unit dosage for parenteral administration.

The dose of the amorphous form of Compound 1 to be administered to a subject is rather widely variable and can be subject to the judgment of a health-care practitioner. In general, the amorphous form of Compound 1 can be administered one to seven times a week, once every two weeks, once every three weeks or once every four weeks in a dose of about 0.005 mg/kg of a subject's body weight to about 10 mg/kg of a subject's body weight in a subject, but the above dosage may be properly varied depending on the age, body weight and medical condition of the subject and the type of administration. In one embodiment, the dose is about 0.01 mg/kg of a subject's body weight to about 5 mg/kg of a subject's body weight, about 0.05 mg/kg of a subject's body weight to about 1 mg/kg of a subject's body weight, about 0.1 mg/kg of a subject's body weight to about 0.75 mg/kg of a subject's body weight or about 0.25 mg/kg of a subject's body weight to about 0.5 mg/kg of a subject's body weight. In one embodiment, one dose is given per week. In others, one dose is given two, three or four times per week. In still others, one dose is given per two weeks, per three weeks or per four weeks. In any given case, the amount of the amorphous form of Compound 1 administered will depend on such factors as the solubility of the active component, the formulation used and the route of administration.

In another embodiment, provided herein are methods for the treatment or prevention of a disease or disorder comprising the administration of about 0.375 mg/dose to about 750 mg/dose, about 0.75 mg/dose to about 375 mg/dose, about 3.75 mg/dose to about 75 mg/dose, about 7.5 mg/dose to about 55 mg/dose or about 18 mg/dose to about 37 mg/dose of the amorphous form of Compound 1 to a subject in need thereof.

In another embodiment, provided herein are methods for the treatment or prevention of a disease or disorder comprising the administration of about 1 mg/dose to about 1200 mg/dose, about 10 mg/dose to about 1200 mg/dose, about 100 mg/dose to about 1200 mg/dose, about 400 mg/dose to about 1200 mg/dose, about 600 mg/dose to about 1200 mg/dose, about 400 mg/dose to about 800 mg/dose or about 600 mg/dose to about 800 mg/dose of the amorphous form of Compound 1 to a subject in need thereof. In a particular embodiment, the methods disclosed herein comprise the administration of 400 mg/dose, 600 mg/dose or 800 mg/dose of the amorphous form of Compound 1 to a subject in need thereof. In a particular embodiment, the methods disclosed herein comprise the administration of 20 mg/dose, 40 mg/dose, 80 mg/dose, 160 mg/dose, 320 mg/dose or 650 mg/dose of the amorphous form of Compound 1 to a subject in need thereof.

In another embodiment, provided herein are unit dosage formulations that comprise between about 1 mg and 200 mg, about 35 mg and about 1400 mg, about 125 mg and about 1000 mg, about 250 mg and about 1000 mg, or about 500 mg and about 1000 mg of the amorphous form of Compound 1.

In a particular embodiment, provided herein are unit dosage formulations comprising about 100 mg or 400 mg of the amorphous form of Compound 1. In a particular embodiment, provided herein are unit dosage formulations comprising about 20 mg, about 40 mg, about 80 mg, about 160 mg, about 320 mg or about 650 mg of the amorphous form of Compound 1.

In another embodiment, provided herein are unit dosage formulations that comprise 1 mg, 5 mg, 10 mg, 15 mg, 20 mg, 30 mg, 35 mg, 40 mg, 50 mg, 70 mg, 80 mg, 100 mg, 125 mg, 134 mg, 140 mg, 160 mg, 175 mg, 200 mg, 250 mg, 280 mg, 320 mg, 350 mg, 500 mg, 560 mg, 637 mg, 650 mg, 700 mg, 750 mg, 805 mg, 1000 mg or 1400 mg of the amorphous form of Compound 1.

The amorphous form of Compound 1 can be administered once, twice, three, four or more times daily. In a particular embodiment, doses of 600 mg or less are administered as a once daily dose and doses of more than 600 mg are administered twice daily in an amount equal to one half of the total daily dose.

In another embodiment, provided herein are compositions comprising an effective amount of the amorphous form of Compound 1 and a pharmaceutically acceptable carrier or vehicle, wherein a pharmaceutically acceptable carrier or vehicle can comprise an excipient, diluent, or a mixture thereof. In one embodiment, the composition is a pharmaceutical composition.

The compositions can be in the form of solutions, parenteral solutions, and suspensions and the like. Compositions can be formulated to contain a single dose, or a convenient fraction of a single dose, in a dosage unit, which may be a single vial or convenient volume of a liquid. In one embodiment, the solutions are prepared from water-soluble salts, such as the hydrochloride salt. In general, all of the compositions are prepared according to known methods in pharmaceutical chemistry.

The effect of the amorphous form of Compound 1 can be delayed or prolonged by proper formulation. The parenteral preparations can be made long-acting, by dissolving or suspending the amorphous form of Compound 1 in oily or emulsified vehicles that allow it to disperse slowly in the serum.

In one embodiment, provided herein is a pharmaceutical composition comprising about 0.1-5% by weight of the amorphous form of Compound 1, about 50-80% by weight of polyethylene glycol (PEG), about 5-30% by weight of ethanol (EtOH) and about 15-45% by weight of saline. In certain embodiments, pharmaceutical compositions provided herein contain about 0.05%, about 0.1%, about 0.2%, about 0.4%, about 0.8% or about 1.63% by weight of the amorphous form of Compound 1.

In one embodiment, provided herein are pharmaceutical compositions comprising amorphous form of Compound 1 reconstituted in a solution comprising about 54% by weight of PEG, about 18% by weight of EtOH and about 28% by weight of saline. In certain embodiments, the reconstituted solution comprises about 1-3% by weight of the amorphous form of Compound 1. In certain embodiments, the reconstituted solution comprises about 0.05%, about 0.1%, about 0.2%, about 0.4%, about 0.8% or about 1.63% by weight of the amorphous form of Compound 1. In a particular embodiment, the reconstituted solution is administered at a volume of about 40 mL.

In one embodiment, provided herein are pharmaceutical compositions comprising amorphous form of Compound 1 reconstituted in a solution comprising about 54.1% by weight of PEG, about 17.7% by weight of EtOH and about 28.2% by weight of saline. In certain embodiments, the reconstituted solution comprises about 1-3% by weight of the amorphous form of Compound 1. In certain embodiments, the reconstituted solution comprises about 0.05%, about 0.1%, about 0.2%, about 0.4%, about 0.8% or about 1.63% by weight of the amorphous form of Compound 1. In a particular embodiment, the reconstituted solution is administered at a volume of about 40 mL.

In one embodiment, provided herein are pharmaceutical compositions comprising amorphous form of Compound 1 reconstituted in a solution comprising about 65.6% by weight of PEG, about 10.5% by weight of EtOH and about 23.9% by weight of saline. In certain embodiments, the reconstituted solution comprises about 1-3% by weight of the amorphous form of Compound 1. In certain embodiments, the reconstituted solution comprises about 1.7% by weight of the amorphous form of Compound 1.

In one embodiment, provided herein are pharmaceutical compositions comprising about 0.1 mg to about 1500 mg of the amorphous form of Compound 1 in about 0.5 g to about 100 g of liquid which comprises about 0 g to about 60 g of PEG, about 0 g to about 20 g of EtOH and about 0 g to about 20 g of saline. In certain embodiments, pharmaceutical compositions provided herein contain about 20 mg, about 40 mg, about 80 mg, about 160 mg, about 320 mg or about 650 mg of the amorphous form of Compound 1.

In one embodiment, provided herein are pharmaceutical compositions comprising about 0.1 mg to about 1500 mg of the amorphous form of Compound 1 in about 0.5 g to about 100 g of liquid which comprises about 1 g to about 60 g of PEG, about 1 g to about 20 g of EtOH and about 1 g to about 20 g of saline. In certain embodiments, pharmaceutical compositions provided herein contain about 20 mg, about 40 mg, about 80 mg, about 160 mg, about 320 mg or about 650 mg of the amorphous form of Compound 1.

In one embodiment, provided herein are pharmaceutical compositions comprising about 0.1 mg to about 750 mg of the amorphous form of Compound 1 in about 0.5 g to about 100 g of liquid which comprises about 0 g to about 80 g of PEG, about 0 g to about 20 g of EtOH and about 0 g to about 20 g of saline.

In one embodiment, provided herein are pharmaceutical compositions comprising about 0.1 mg to about 750 mg of the amorphous form of Compound 1 in about 0.5 g to about 100 g of liquid which comprises about 1 g to about 60 g of PEG, about 1 g to about 20 g of EtOH and about 1 g to about 20 g of saline.

In one embodiment, provided herein are pharmaceutical compositions comprising about 500 mg to about 1000 mg of the amorphous form of Compound 1 in about 3 g to about 75 g of liquid which comprises about 10 g to about 50 g of PEG, about 1 g to about 10 g of EtOH and about 5 g to about 15 g of saline.

In one embodiment, provided herein are pharmaceutical compositions comprising about 50 mg to about 300 mg of the amorphous form of Compound 1 in about 15 g to about 75 g of liquid which comprises about 10 g to about 50 g of PEG, about 1 g to about 10 g of EtOH and about 5 g to about 15 g of saline.

In one embodiment, provided herein are pharmaceutical compositions comprising about 0.1 mg to about 750 mg of the amorphous form of Compound 1 in about 25 g to about 55 g of liquid comprising about 15 g to about 40 g of PEG, about 2.5 g to about 5.5 g of EtOH and about 7.5 g to about 9.5 g of saline.

In one embodiment, provided herein are pharmaceutical compositions comprising about 50 mg to about 300 mg of the amorphous form of Compound 1 in about 25 g to about 45 g of liquid comprising about 15 g to about 30 g of PEG, about 2.5 g to about 5.5 g of EtOH and about 7.5 g to about 9.5 g of saline.

In one embodiment, provided herein are pharmaceutical compositions comprising about 10 mg to about 500 mg of the amorphous form of Compound 1 in about 3.5 g to about 20 g of liquid which comprises about 1 g to about 10 g of PEG, about 0.1 g to about 5 g of EtOH and about 0.5 g to about 5 g of saline.

In one embodiment, provided herein are pharmaceutical compositions comprising about 50 mg to about 200 mg of the amorphous form of Compound 1 in about 6 g to about 11 g of liquid comprising about 4.5 g to about 6.5 g of PEG, about 0.5 g to about 1.5 g of EtOH and about 1.0 g to about 2.5 g of saline.

In one embodiment, provided herein are pharmaceutical compositions comprising about 637 mg of the amorphous form of Compound 1, about 24.3 g of PEG, about 3.9 g of EtOH and about 8.9 g of saline.

In one embodiment, provided herein are pharmaceutical compositions comprising the amorphous form of Compound 1 (e.g., about 637 mg or about 134 mg) and about 26.3 g of PEG, about 4.2 g of EtOH and about 9.6 g of saline.

In certain embodiments, the pharmaceutical compositions provided herein comprise about 0.1 mg/mL to about 20 mg/mL of the amorphous form of Compound 1.

In one embodiment, provided herein are pharmaceutical compositions comprising 0.1 mg/mL to about 20 mg/mL of the amorphous form of Compound 1 in about 0.5 g to about 100 g of liquid which comprises about 0 g to about 60 g of PEG, about 0 g to about 20 g of EtOH and about 0 g to about 20 g of saline. In certain embodiments, pharmaceutical compositions provided herein contain about 20 mg, about 40 mg, about 80 mg, about 160 mg, about 320 mg or about 650 mg of the amorphous form of Compound 1.

In one embodiment, provided herein are pharmaceutical compositions comprising 0.1 mg/mL to about 20 mg/mL of the amorphous form of Compound 1 in about 0.5 g to about 100 g of liquid which comprises about 1 g to about 60 g of PEG, about 1 g to about 20 g of EtOH and about 1 g to about 20 g of saline. In certain embodiments, pharmaceutical compositions provided herein contain about 20 mg, about 40 mg, about 80 mg, about 160 mg, about 320 mg or about 650 mg of the amorphous form of Compound 1.

In certain embodiments, PEG used in the pharmaceutical compositions herein has a molecular weight of about 300 g/mol to about 1000 g/mol. In certain embodiments, PEG used in the pharmaceutical compositions herein is PEG-300.

In certain embodiments, the pharmaceutical compositions provided herein comprise the amorphous form of Compound 1, including the substantially pure amorphous form of Compound 1.

6. EXAMPLES

The following Examples are presented by way of illustration, not limitation. The following abbreviations are used in descriptions and examples:

DSC: Differential Scanning calorimetry

EtOH: Ethanol

HPLC: High performance liquid chromatography

PEG Polyethylene glycol

XRPD: X-Ray Powder Diffraction

6.1 Analytical Methods

Solid samples were analyzed by XRPD. XRPD analysis was conducted on a PANalytical Empyrean or a Thermo ARL X'TRA X-ray powder diffractometer using Cu Kα radiation at 1.54 Å.

The PANalytical Empyrean instrument was equipped with a fine focus X-ray tube. The voltage and amperage of the X-ray generator were set at 45 kV and 40 mA, respectively. The divergence slits were set at $\frac{1}{16}°$ and $\frac{1}{8}°$, and the receiving slits was set at $\frac{1}{16}°$. Diffracted radiation was measured using a Pixel 2D detector. A theta-two theta continuous scan was set at step size 0.013 or 0.026 from 3° to 40° 2θ with sample spinning rate at 4. A sintered alumina standard was used to check the peak positions.

The Thermo ARL X'TRA instrument was equipped with a fine focus X-ray tube. The voltage and amperage of the X-ray generator were set at 45 kV and 40 mA, respectively. The divergence slits were set at 4 mm and 2 mm and the measuring slits were set at 0.5 mm and 0.2 mm. Diffracted radiation was measured using a Peltier-cooled Si (Li) solid-state detector. A theta-two theta continuous scan at 2.40°/min (0.5 sec/0.02° step) from 1.5° to 40° 2θ was used. A sintered alumina standard was used to check the peak positions.

DSC analyses were performed on a TA Discovery Differential Scanning calorimeter. Indium was used as the calibration standard. Approximately 2-5 mg of sample was placed into a DSC pan. The sample was heated under nitrogen at a rate of 10° C./min, up to a final temperature of 300° C. Melting points were reported as the extrapolated onset temperatures.

Morphology analysis of the samples was carried out on an Even Mini SEM. Small amounts of samples were dispersed on a sample holder, and then coating with gold and viewed with 500× magnification.

6.2 Preparation of Amorphous Form

An amorphous form of Compound 1 was obtained from a spray-drying process of Compound 1 as depicted in FIG. 5. The spray-drying process comprised: (1) mixing Compound 1 with methanol at 25° C. to yield a suspension; (2) heating to 121° C.; (3) spray-drying under the conditions in Table 1 or Table 2 to yield an amorphous solid form; and (4) collecting the resulting solids. Alternatively, the spray drying process comprised: (1) mixing Compound 1 with acetone to yield a solution; (2) spray-drying under the conditions in Table 3 to yield an amorphous solid form; and (3) collecting the resulting solids. It was found that the resulting amorphous form of Compound 1 is readily soluble in ethanol.

TABLE 1

Spray-drying condition A

| Formulation | 100% Compound 1 at 5 wt % solids in 100% MeOH |
|---|---|
| Batch Size (g) | 346.7 |
| Atomizer | Flash Atomizer ID = 380 μm |
| Spray Solution Temperature (° C.) | 121 |
| Solution Flow Rate (g/min) | 96 |
| Atomization Pressure (Psi)* | 220 |
| Drying Gas Flow Rate (g/min) | 1300 |
| Inlet Temperature (° C.) | 138 |
| Outlet Temperature (° C.) | 48 |
| Cyclone Size | High Efficiency = 3" (Standard = 6") |
| Wet Yield (%) | 79 |
| Dry Yield (%)** | 74 |
| Bulk Packaged SDP (g) | 215.3 |
| Secondary Drying | Convection Tray Dryer at 40° C. and 15% RH for 21 Hr |

*Atomization pressure rose steadily throughout the run
**Dry yield includes the dried bulk and the dry SDP samples only

TABLE 2

Spray-drying condition B

| Formulation | 100% Compound 1 Sprayed at 5 wt % Solids in MeOH |
|---|---|
| Atomizer | Schlick 2.0 |
| Atomization Pressure (Psi) | 120 |
| Solution Flow Rate (g/min) | 25 |
| Solution Temperature (° C.) | 121 |
| Drying Gas Flow Rate (g/min) | 500 |
| Inlet Temperature (° C.) | 145 |
| Outlet Temperature (° C.) | 50 |
| Process Yield (%) | 82.1 |
| Outlet RS (%) | 6.73 |

TABLE 3

Spray-drying condition C

| Formulation | 100% Compound 1 at 0.17 wt % solids in acetone |
|---|---|
| Solids Batch Size (g) | 5 |
| Solution Temperature (° C.) | Room temperature (15-27° C.) |
| Atomizer | Spraying Systems ¼ J Series 2850 Liquid Cap - 64 Air Cap |
| Atomization Pressure (Psi) | 7 |
| Solution Feed Rate (g/min) | 32 |
| Solution Temperature (° C.) | 121 |
| Drying Gas Flow Rate (g/min) | 450 |
| Inlet Temperature (° C.) | 90 |
| Outlet Temperature (° C.) | 43 |
| Wet Yield (%) | 83.3 |

The amorphous form XRPD contains no crystalline diffraction patterns and has halo, which is typical for amorphous compounds, as shown in FIG. 1. Representative DSC thermograms of amorphous Compound 1 are shown in FIG. 2A and FIG. 2B, showing representative glass transition and/or melting temperatures.

FIG. 3A and FIG. 3B are representative SEM images of amorphous Compound 1.

Representative particle size distribution patters for amorphous Compound 1 are shown in FIG. 4A, FIG. 4B and FIG. 4C.

A stability study indicated that the amorphous form is chemically and physically stable over three months either in its HPLC purity as depicted in FIG. 6 or in its XRPD as depicted in FIG. 7.

6.3 Dissolution of Amorphous Form

Dissolution times for the amorphous form of Compound 1 under certain conditions are provided in Table 4.

TABLE 4

Dissolution times of the amorphous solid form of Compound 1.

| Reconstitution formulation | Dissolution Time |
|---|---|
| #1 (4.6 mL EtOH added to 700 mg amorphous Compound 1), #2 (26.3 mL (25.1:1.2) PEG-300:Ethanol), #3 (10.3 mL Saline) | 1 min |
| 17 mg amorphous Compound 1, 0.105 g EtOH, 0.656 g PEG-300, 0.239 g Saline | 1 min |
| #1 PEG-300/EtOH, #2 Saline | 9 min |

6.4 Formulations of Amorphous Form

Formulations containing the amorphous form of Compound 1 and dosage amounts are provided in Table 5, Table 6 and Table 7.

TABLE 5

Formulations A and B.

| Final solution after Reconstitution | Final Concentration at Injection | Final Volume of Formulations A and B | | Total Dose Based on 50 mL Slow Push |
|---|---|---|---|---|
| | | A | B | |
| 65.6% PEG-300 10.5% EtOH 23.9% Saline | 17.2 mg/g 16.1 mg/mL | 39.6 mL | 8.3 mL | 805 mg/dose |

TABLE 6

Additional Formulations

| Component | Volume % (vol/40 mL dose) | Wt. % (wt/40 mL dose) |
|---|---|---|
| Saline | 25% (10 mL) | 28.2% (12.6 g) |
| PEG-300 | 61% (24.4 mL) | 54.1% (24.1 g) |
| Ethanol | 14% (5.6 mL) | 17.7% (7.9 g) |

TABLE 7

Dosage amounts

| Dose (mg) | Total Volume (mL) | Percent active |
|---|---|---|
| 20 | 40 | 0.05% |
| 40 | 40 | 0.1% |
| 80 | 40 | 0.2% |
| 160 | 40 | 0.4% |
| 320 | 40 | 0.8% |
| 650 | 40 | 1.63% |

6.1 Dose Preparation Procedure for Amorphous Compound 1

Reconstitution Procedure

TABLE 8

Drug product intermediate (DPI) vial and reconstitution kit

| Vial # | Cap | Amount in Vial | Amount to Reconstitute | Vial Contents |
|---|---|---|---|---|
| DPI vial (To be stored under refrigerated conditions 2-8° C.) | | | | |
| Vial 1 | Yellow | 700 mg | 700 mg | the "Mother" Vial with DPI powder |
| Reconstitution Kit (To be stored under controlled room temperature) | | | | |
| Vial 2 | Blue | 5 ml | 4.6 ml | Ethanol |
| Vial 3 | Green | 40 ml | 26.3 ml | PEG/Ethanol |
| Vial 4 | Red | 50 ml | 10.3 ml | Saline |
| Vial 5 | Magenta | 50 ml | Variable | QS Solution #1 (PEG/Ethanol/Saline Solution) |
| Vial 6 | Magenta | 50 ml | Variable | QS Solution #2 (PEG/Ethanol/Saline Solution) |
| Vial 7 | White | empty | — | Sterile Mixing and Administration |

All reconstitution should be performed under an ISO class 5 air quality environment and Biological safety cabinet. All syringes used must be sterile. Needles in this procedure are either 16 G 1 inch or 18 G 1 inch Precision Glide needle. All vial stoppers must be disinfected with 70% isopropyl alcohol before penetration. Site specific procedures for aseptic drug preparation should be followed. Remove DPI vial from refrigeration and allow to come to controlled room temperature for 10 minutes prior to start of steps below.

Using a 18 G needle, insert into vial 2, invert the vial, and withdraw 4.6 ml Ethanol. Remove the syringe with needle from vial 2 and Inject the ethanol into vial 1, making sure to withdraw equal volume of air from the vial 1 at the end to balance pressure inside the vial. Remove the syringe with needle from vial 1 and shake vigorously, dislodging any powder from the walls of the vial. Shake vigorously up and down for approximately 3 minutes until a white precipitate evenly coats the walls of the vial. Using a 16 G needle insert into vial 3, invert the vial, and withdraw 26.3 ml of PEG/Ethanol. Remove the syringe with needle from vial 3, insert into vial 1 and inject the solution into the white precipitate. Swirl vial 1 to dislodge all white precipitate from the walls of the vial. Then, shake vigorously up and down for a minimum of 5 minutes, until the solids are completely dissolved. Attach a syringe with 18 G needle to the vial 4, invert the vial, and withdraw 10.3 ml saline. Remove the syringe with needle from vial 4, attach the syringe with needle to the vial 1 and inject directly into the solution. Make sure to withdraw equal volume of air from the vial 1 at the end to balance pressure inside the vial 1. NOTE: There will be an initial crash out in the solution, this is expected and should become clear on shaking, the vial will also become warm during this process. Immediately after injection, remove the syringe with needle and shake vigorously up and down for approximately 3 minutes. The solution should remain clear. NOTE: Micro bubbles may be present, this is expected. Attach a syringe with 16 G needle to vial 1, invert vial 1, and withdraw appropriate amount of solution from vial 1 (the Mother Vial) according to the dose outlined in the table below.

TABLE 9

Dose preparations

| Dose (mg) | Volume from Mother Vial (ml) | Volume QS Solution (ml) |
|---|---|---|
| 20 | 1.2 | 38.8 |
| 40 | 2.4 | 37.6 |
| 80 | 4.7 | 35.3 |
| 160 | 9.4 | 30.6 |
| 320 | 18.8 | 21.2 |
| 650 | 38.2 | 1.8 |

Remove the syringe with needle from vial 1, attach the syringe with needle to the vial 7 and inject the solution into vial 7. Make sure to withdraw equal volume of air from the vial 7 at the end to balance pressure inside the vial 7. Attach a syringe with 16 G needle to the vial 5, invert vial 5, and withdraw the appropriate amount of QS Solution according to the dose outlined by the table above. Remove the syringe with needle from vial 5, insert the syringe with needle to the vial 7 and inject the solution into vial 7. Make sure to withdraw equal volume of air from the vial 7 at the end to balance pressure inside the vial 7. Remove the syringe with needle from vial 7, shake vigorously for 15 seconds to mix. The final volume should be ~40 ml. Attach a syringe with 16 G needle to the vial 7, invert vial 7, and withdraw all 40 ml of final solution.

Subject Administration Procedure

To prevent potential drug precipitation induced by undissolved drug particles, the final solution should be administered to the subject through the 0.2 μm in-line filter as soon as possible and no later than 8 hours and be kept at the controlled room temperature (15° C.-30° C.) for transportation between sites after "Reconstitution Procedure" above. Remove the syringe from vial 7 and place onto an syringe pump. Attach a 0.2 micron Ultrasite Filtered Extension Set to the syringe for administration to subject. Prime the tubing prior to the infusion. Flush the patient line with the QS solution from Vial 6. Set the pump for administration of entire 40 ml final solution over 1 hour. After administration, flush the patient line with QS Solution from vial 6.

The embodiments disclosed herein are not to be limited in scope by the specific embodiments disclosed in the examples which are intended as illustrations of a few aspects of the disclosed embodiments and any embodiments that are functionally equivalent are encompassed by the present disclosure. Indeed, various modifications of the embodiments disclosed herein are in addition to those shown and described herein will become apparent to those skilled in the art and are intended to fall within the scope of the appended claims.

A number of references have been cited, the disclosures of which are incorporated herein by reference in their entirety.

Compounds of the invention are for use in the methods of treatment provided herein.

What is claimed is:

1. An amorphous form of Compound 1, or a tautomer thereof:

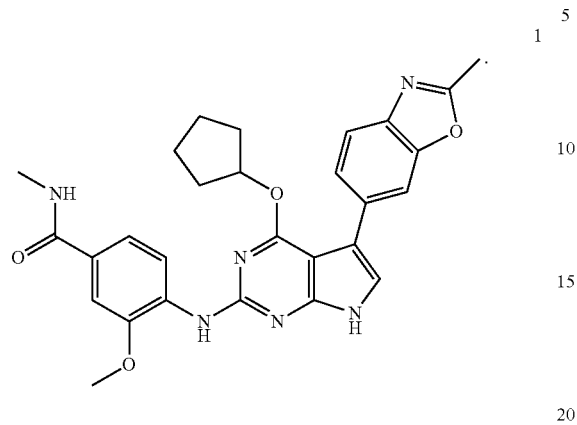

2. The amorphous form of claim 1 which is anhydrous.

3. The amorphous form of claim 1 which is no less than about 95% pure with respect to other solid forms.

4. A pharmaceutical composition comprising about 0.1-5% by weight of the amorphous form of claim 1, about 50-80% by weight of polyethylene glycol (PEG), about 5-30% by weight of ethanol (EtOH) and about 15-45% by weight of saline.

5. A pharmaceutical composition comprising about 0.1 mg to about 1500 mg of the amorphous form of claim 1, in about 0.5 g to about 100 g of liquid which comprises about 1 g to about 60 g of PEG, about 1 g to about 20 g of EtOH and about 1 g to about 20 g of saline.

* * * * *